US008734446B2

(12) United States Patent
Miller

(10) Patent No.: US 8,734,446 B2
(45) Date of Patent: May 27, 2014

(54) EXTERNAL FIXATION SURGICAL CLAMP WITH SWIVEL

(75) Inventor: Stephen T. Miller, Scotts Valley, CA (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/271,483

(22) Filed: Oct. 12, 2011

(65) Prior Publication Data
US 2012/0095462 A1 Apr. 19, 2012

Related U.S. Application Data

(60) Provisional application No. 61/392,228, filed on Oct. 12, 2010, provisional application No. 61/392,256, filed on Oct. 12, 2010.

(51) Int. Cl.
A61B 17/64 (2006.01)
(52) U.S. Cl.
USPC .............................. 606/59; 606/277; 606/324
(58) Field of Classification Search
USPC .............. 606/54–59, 250–253, 277, 278, 324
See application file for complete search history.

(56) References Cited

U.S. PATENT DOCUMENTS

| 1,706,215 | A | 3/1929 | Davidson |
| 2,705,603 | A | 4/1955 | Bitz et al. |
| 3,044,512 | A | 7/1962 | Jones |
| 3,154,331 | A | 10/1964 | Engelhardt |
| 3,373,465 | A | 3/1968 | Johnson et al. |
| 3,406,987 | A | 10/1968 | Hunder et al. |
| 4,037,978 | A | 7/1977 | Connelly |
| 4,115,966 | A | 9/1978 | DeLee |
| 4,312,488 | A | 1/1982 | Pierron |
| 4,388,747 | A | 6/1983 | Plummer |
| 4,483,334 | A | 11/1984 | Murray |
| 4,620,533 | A | 11/1986 | Mears |

(Continued)

FOREIGN PATENT DOCUMENTS

DE 2430234 1/1975
EP 1820461 8/2007

(Continued)

OTHER PUBLICATIONS

Swiss Patent Office, Application No. 03 891/90-6, titled "Fixateur externe," Applicant—Jaquet Orthopedie S.A., filed Dec. 16, 1991, 34 pages.

(Continued)

Primary Examiner — Jerry Cumberledge
(74) Attorney, Agent, or Firm — Schwegman Lundberg & Woessner, P.A.

(57) ABSTRACT

A clamping device for an external fixation system includes a first clamp having an opening for receiving an external fixation element, the first clamp having an axle seat. A first base component includes a concave first surface and a second surface facing away from the first surface. The concave first surface is in selective engagement with the clamp. A swivel element comprises an axle component and a post component. The axle component is disposed on the axle seat of the first clamp. The post component extends from the axle component and has a length sized to extend from the axle component through a second external fixation clamp. The post component is arranged to swivel relative to the axle seat. Methods are also disclosed.

32 Claims, 18 Drawing Sheets

(56) References Cited

U.S. PATENT DOCUMENTS

| | | | |
|---|---|---|---|
| 4,653,481 A | 3/1987 | Howland et al. | |
| 4,662,365 A | 5/1987 | Gotzen et al. | |
| 4,700,437 A | 10/1987 | Hoshino | |
| D295,725 S | 5/1988 | Shioda | |
| 4,817,897 A | 4/1989 | Kreusel | |
| 5,312,405 A | 5/1994 | Korotko et al. | |
| 5,427,465 A | 6/1995 | Sato | |
| 5,662,648 A | 9/1997 | Faccioli et al. | |
| 5,683,389 A | 11/1997 | Orsak | |
| 5,709,681 A | 1/1998 | Pennig | |
| 5,727,899 A | 3/1998 | Dobrovolny | |
| 5,741,252 A | 4/1998 | Mazzio et al. | |
| 5,746,741 A | 5/1998 | Kraus et al. | |
| 5,752,954 A * | 5/1998 | Mata et al. | 606/59 |
| 5,800,548 A | 9/1998 | Martin et al. | |
| 5,827,282 A | 10/1998 | Pennig | |
| 5,860,728 A | 1/1999 | Maglica | |
| 5,891,144 A | 4/1999 | Mata et al. | |
| 5,976,141 A | 11/1999 | Haag et al. | |
| 6,022,348 A | 2/2000 | Spitzer | |
| 6,080,153 A | 6/2000 | Mata et al. | |
| 6,102,911 A | 8/2000 | Faccioli et al. | |
| 6,217,577 B1 | 4/2001 | Hofmann | |
| 6,264,396 B1 | 7/2001 | Dobrovolny | |
| 6,277,069 B1 | 8/2001 | Gray | |
| 6,376,775 B1 | 4/2002 | Leijon et al. | |
| 6,386,786 B1 | 5/2002 | Perlman et al. | |
| 6,409,729 B1 * | 6/2002 | Martinelli et al. | 606/59 |
| 6,500,177 B1 | 12/2002 | Martinelli et al. | |
| 6,637,082 B1 | 10/2003 | Chang | |
| 6,652,523 B1 | 11/2003 | Evrard et al. | |
| 6,702,814 B2 | 3/2004 | Walulik et al. | |
| 6,716,212 B1 | 4/2004 | Pickens | |
| 6,736,775 B2 | 5/2004 | Phillips | |
| 6,887,197 B2 | 5/2005 | Phillips | |
| 7,004,943 B2 * | 2/2006 | Ferrante et al. | 606/59 |
| 7,048,735 B2 | 5/2006 | Ferrante et al. | |
| 7,241,071 B2 | 7/2007 | Carraher et al. | |
| 7,241,074 B2 * | 7/2007 | Thomke et al. | 403/385 |
| 7,261,713 B2 | 8/2007 | Langmaid | |
| 7,314,331 B1 | 1/2008 | Koros et al. | |
| 7,320,556 B2 | 1/2008 | Vagn-Erik | |
| 7,449,023 B2 * | 11/2008 | Walulik et al. | 606/59 |
| 7,473,223 B2 | 1/2009 | Fetzer | |
| 7,491,008 B2 | 2/2009 | Thomke et al. | |
| 7,527,626 B2 | 5/2009 | Lutz et al. | |
| 7,562,855 B2 | 7/2009 | Oetlinger | |
| 7,588,537 B2 | 9/2009 | Bass | |
| 7,708,736 B2 | 5/2010 | Mullaney | |
| 7,744,632 B2 | 6/2010 | Usher | |
| 7,887,537 B2 | 2/2011 | Ferrante et al. | |
| 7,931,650 B2 | 4/2011 | Winquist et al. | |
| 7,938,829 B2 | 5/2011 | Mullaney | |
| 8,147,491 B2 * | 4/2012 | Lavi | 606/59 |
| 8,172,840 B2 * | 5/2012 | Murner et al. | 606/54 |
| 8,241,285 B2 * | 8/2012 | Mullaney | 606/59 |
| 2001/0004432 A1 | 6/2001 | Pfister | |
| 2002/0037193 A1 | 3/2002 | Gibbons et al. | |
| 2002/0042613 A1 | 4/2002 | Mata | |
| 2002/0061225 A1 | 5/2002 | Boucher et al. | |
| 2002/0165543 A1 | 11/2002 | Winquist et al. | |
| 2003/0149429 A1 | 8/2003 | Ferrante et al. | |
| 2005/0113831 A1 | 5/2005 | Franck et al. | |
| 2006/0017566 A1 | 1/2006 | Gauvreau et al. | |
| 2006/0039750 A1 | 2/2006 | Thomke | |
| 2006/0229602 A1 | 10/2006 | Olsen | |
| 2006/0229603 A1 | 10/2006 | Olsen | |
| 2006/0255521 A1 | 11/2006 | Brunner | |
| 2006/0271045 A1 | 11/2006 | Hubbard et al. | |
| 2006/0287652 A1 | 12/2006 | Lessig et al. | |
| 2007/0038217 A1 * | 2/2007 | Brown et al. | 606/57 |
| 2007/0043355 A1 * | 2/2007 | Bette et al. | 606/61 |
| 2007/0049932 A1 | 3/2007 | Richelsoph et al. | |
| 2007/0198012 A1 | 8/2007 | Thomke et al. | |
| 2007/0293860 A1 | 12/2007 | Oesch | |
| 2008/0065068 A1 | 3/2008 | Thomke et al. | |
| 2008/0215053 A1 | 9/2008 | Thomke et al. | |
| 2009/0036891 A1 | 2/2009 | Brown et al. | |
| 2009/0088751 A1 | 4/2009 | Mullaney | |
| 2009/0299368 A1 | 12/2009 | Bauer | |
| 2011/0066151 A1 * | 3/2011 | Murner et al. | 606/54 |
| 2011/0098706 A1 | 4/2011 | Mullaney | |
| 2011/0098707 A1 | 4/2011 | Mullaney | |
| 2011/0172663 A1 | 7/2011 | Mullaney | |
| 2012/0004659 A1 | 1/2012 | Miller et al. | |
| 2012/0089142 A1 | 4/2012 | Mullaney et al. | |

FOREIGN PATENT DOCUMENTS

| | | |
|---|---|---|
| EP | 2294994 | 3/2011 |
| EP | 2294994 A1 | 3/2011 |
| WO | WO-89/05126 | 6/1989 |
| WO | WO-90/11055 | 10/1990 |
| WO | WO-92/12683 | 8/1992 |
| WO | WO-98/51227 | 11/1998 |
| WO | WO-99/25264 | 5/1999 |
| WO | WO-03065911 | 8/2003 |
| WO | WO-2009/004347 | 1/2009 |
| WO | WO-2012051255 | 4/2012 |

OTHER PUBLICATIONS

European Patent Office, International Search Report and Written Opinion dated Oct. 13, 2011, Application No. PCT/US2011/042813, 11 pages.

PCT/ISA-US Office, International Search Report and Written Opinion dated Dec. 2, 2008, Application No. PCT/US08/77800, 11 pages.

European Patent Office, International Search Report and Written Opinion mailed Mar. 28, 2012, Application No. PCT/US2011/963985, 10 pages.

European Patent Office, International Search Report and Written Opinion mailed Mar. 20, 2012, Application No. PCT/US2011/059303, 13 pages.

European Patent Office, International Search Report and Written Opinion mailed Apr. 10, 2012, Application No. PCT/US2011/063976, 8 pages.

European Patent Office, International Search Report and Written Opinion mailed Jan. 9, 2012, Application No. PCT/US2011/055907, 9 pages.

"European Application Serial No. 11774150.4, Office Action mailed Jun. 14, 2013", 2 pgs.

"International Application Serial No. PCT/US2011/055907, International Preliminary Report on Patentability mailed Apr. 19, 2013", 7 pgs.

"International Application Serial No. PCT/US2011/055907, International Search Report mailed Jan. 9, 2012", 3 pgs.

"International Application Serial No. PCT/US2011/055907, Written Opinion mailed Jan. 9, 2012", 5 pgs.

* cited by examiner

# EXTERNAL FIXATION SURGICAL CLAMP WITH SWIVEL

PRIORITY

This application claims priority to U.S. Provisional Patent Application 61/392,228, titled Multi-Pin Surgical Clamp with Swivel, filed Oct. 12, 2010 and U.S. Provisional Patent Application 61/392,256, titled Surgical Clamp with Swivel, filed Oct. 12, 2010, both of which are incorporated herein by reference.

FIELD OF THE INVENTION

This application is directed to a surgical clamp for an external fixation system, where the surgical clamp includes a swivel.

BACKGROUND

External fixation systems are used to stabilize fractured bones or hold bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened.

Some external fixation systems include two-part clamping devices for gripping the structural members. These clamping devices typically include two clamps formed of jaw sets that swivel about a post that runs through both clamps. These clamps allow rotation about the external fixation element, or rotation about the roll axis of each clamp. They also include rotation about the post component, or rotation about the yaw axis of the clamp. One known clamping device includes a ball joint that allows additional rotation about a pitch axis. This device allows the jaw to roll, pitch and yaw on the ball joint while the jaw can also roll about the external fixation element, giving it redundant degrees of freedom. Friction maintains the orientation of the jaw set relative to whatever the jaw set is mounted upon. Another known clamping device includes concave surfaces that guide additional rotation about the pitch axis. Because the jaw set of this clamping device angles relative to the post, the clamping load is reduced to the cosine of the pitch angle. This requires that the designer limit the amount of angulation appropriately.

The present disclosure addresses one or more of the problems found in the prior art.

SUMMARY

The present disclosure is directed, in one aspect, to clamping device for an external fixation system where the post for a first clamp is mounted on an axle located in the second clamp which allows the post and first clamp to rotate about the pitch axis of the second clamp.

In one exemplary aspect, the present disclosure is directed to a clamping device for an external fixation system. The clamping device includes a first clamp having an opening for receiving an external fixation element, the first clamp having an axle seat. A first base component includes a concave first surface and a second surface facing away from the first surface. The concave first surface is in selective engagement with the clamp. A swivel element comprises an axle component and a post component. The axle component is disposed on the axle seat of the first clamp. The post component extends from the axle component and has a length sized to extend from the axle component through a second external fixation clamp. The post component is arranged to swivel relative to the axle seat.

In one aspect, the post component is configured to pivot about the axle component. In another aspect, the first clamp comprises an inner jaw and an outer jaw, and the axle seat is disposed inside the inner jaw.

In one exemplary aspect, the present disclosure is directed to a clamping device for an external fixation system. The clamping device includes a first clamp having an opening for receiving a first external fixation element. The first clamp includes an axle seat. A second clamp includes an opening for receiving a second external fixation element. The clamping device includes a swivel element comprising an axle component and a post component. The axle component is disposed on the axle seat of the first clamp, and the post component extends from the axle component through the second clamp. The post component and the second clamp are arranged to swivel in a single plane relative to the axle seat.

In yet another exemplary aspect, the present disclosure is directed to a clamping device for an external fixation system. The clamping device includes a first clamp comprising a first jaw and a second jaw, the first and second jaws cooperating to capture a fixation element. One of the first and second jaws has a hollow interior portion comprising an axle seat. A second clamp includes a third jaw and a fourth jaw. The third and fourth jaws cooperate to capture a fixation element. A swivel element has an axle disposed in the hollow interior portion on the axle seat and has a post component extending from the hollow interior portion through the second clamp. The second clamp is configured to rotate about an axis coincident with the post, and the second clamp and the post component are configured to rotate about an axis coincident with the axle.

In yet another exemplary aspect, the present disclosure is directed to a method of assembling a fixation frame including the steps of introducing a first fixation element into a first clamp; introducing a second fixation element into a second clamp; pivoting the second clamp relative to the first clamp about pitch axis coincident with an axle associated with the first clamp; and rotating the second clamp relative to the first clamp about a yaw axis coincident with a post extending from the first clamp.

Some components of the clamp may be similar in some respects to components found in U.S. Patent Application Publication No. 2009/0088751 to Mullaney, application Ser. No. 12/238,532, incorporated herein by reference, or may be similar in some respects to components found in U.S. patent application Ser. No. 13/175,343, titled Multi-Locking External Fixation Clamp, filed Jul. 1, 2011, incorporated by reference herein in its entirety.

BRIEF DESCRIPTION OF THE DRAWINGS

Aspects of the present disclosure are best understood from the following detailed description when read with the accompanying figures.

DETAILED DESCRIPTION

Figure 1:
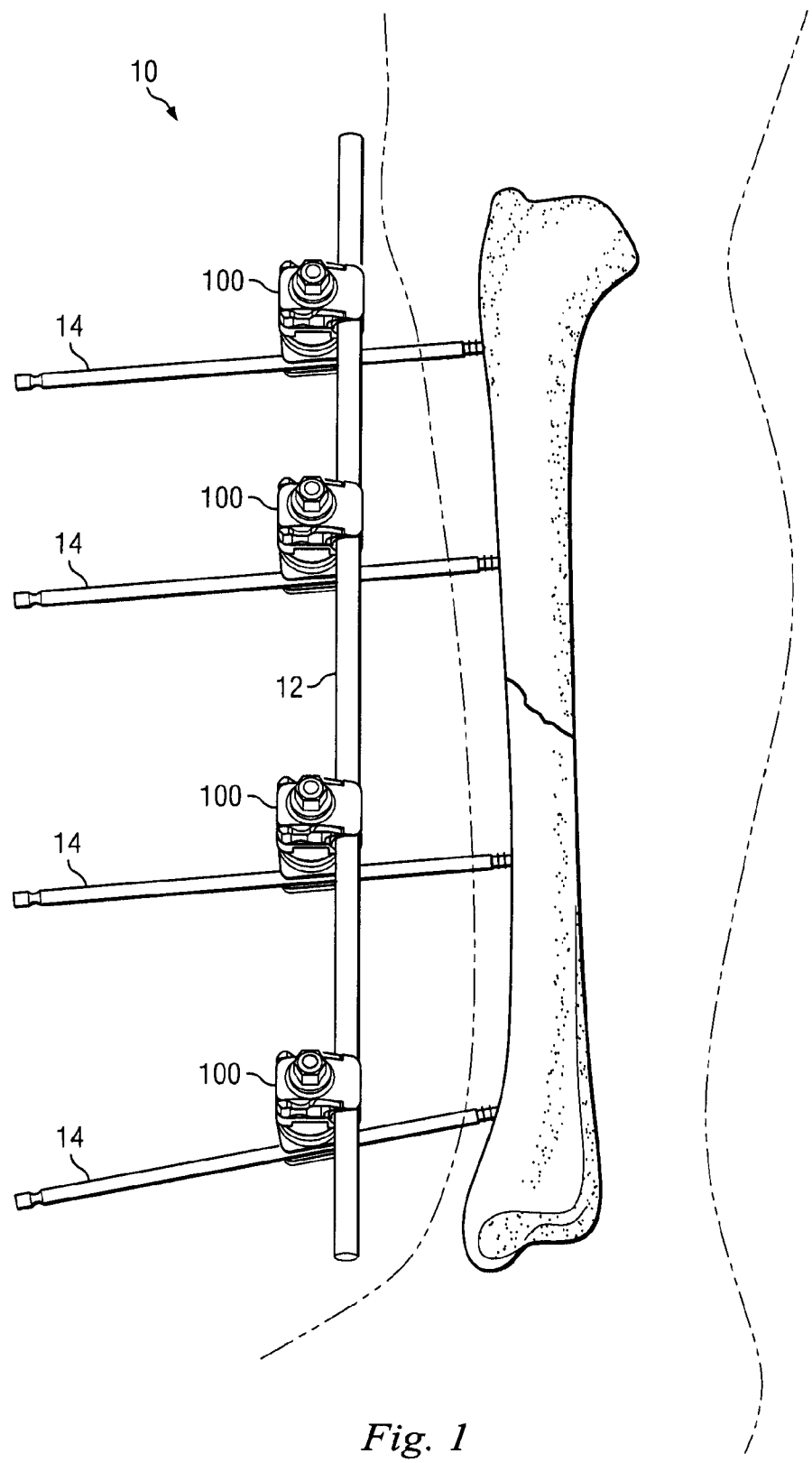
FIG. 1 is an illustration of an exemplary external fixation system in accordance with one exemplary aspect of the present disclosure connected to a patient's bone tissue.

The present disclosure relates generally to the field of external fixation systems, and more particularly to clamping devices for connecting bone pins, wires, rings, struts, bars, rods, or other structural members (referred to collectively as "fixation elements"). For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and/or further modifications in the described embodiments, and any further applications of the principles of these inventions as described herein are contemplated as would normally occur to one skilled in the art to which the disclosure relates.

The external fixation system disclosed herein includes a clamping device having a plurality of clamps, arranged to receive and secure fixation rods or bars (or other fixation elements) and/or pins (or other fixation elements) that extend into and secure patient tissue. These multiple clamps, however, are arranged to pivot relative to each other about an axis coincident with a longitudinally extending post, and also arranged to swivel relative to each other about an axis coincident with a transverse axle. This increases simplicity and efficiency of fixation system setup, providing advantages in configurations not obtainable with known prior systems. For example, one aspect of the disclosure provides a secure locking system by permitting a clamp to rotate, while still maintaining the clamping load aligned in a direction normal to the clamp. Because of this, the amount of angulation can be increased well beyond that which was previously obtainable. Accordingly, a surgeon can manipulate the clamp in a manner that was not previously feasible while still maintaining a suitable locking force on the clamp, resulting in a solid grip on a fixation element.

FIG. 1 shows an exemplary external fixation system 10 attached to a patient's fractured tibia. The system 10 includes rigid bars 12 and plurality of pins 14 drilled into the bone on opposing sides of the fracture. Although this disclosure references bars and pins, it should be understood that any fixation element may be used, including bone pins, wires, rings, struts, bars, rods, or other structural members. In the example in FIG. 1, each pin 14 is received into one of the clamping devices 100 by inserting the pin 14 between facing jaws of a pin clamp of the clamping device 100 as is described further below. Likewise, each bar 12 is received into one of the clamping devices 100 by inserting the bar 12 between facing jaws of a bar clamp of the clamping device 100 as is described further below, to establish the external fixation framework for bone stabilization. In some embodiments, inserting the bar 12 or pin 14 places the clamp in a provisionally locked position about the bar 12 or pin 14. In this position, the respective clamp can be rotated about the bar 12 or pin 14 and may be axially displaced along the bar 12 or pin 14. In addition, at least one of the clamps may rotate about a longitudinal axis of the clamping device 100, and may pitch up or down around the cylindrical axis of a saddle element, while the jaws maintain the bar or pin in the clamp. As remaining pins 14 are connected to the bar 12 using one of the clamping devices 100, the clamping devices may be adjusted to provide angulation and orientation necessary to align the bone for healing. Additional bar-to-bar fixation clamps and/or bar-to-pin fixation clamps may be added to expand and connect the frame as required. Some embodiments include multipin clamps. Once properly created, the frame may be locked by changing the clamp from a provisionally locked condition to the locked condition.

FIGS. 2-5 show an embodiment of a clamping device 100 according to one exemplary aspect of the present disclosure. For convenience in the figures, similar components are labeled with the same reference number, but are distinguished by a suffix, with the suffix "a" identifying components of one clamp and the suffix "b" identifying components of a similar, but separate clamp. References to those components may be made without the use of the suffix.

The exemplary clamping device 100 includes a bar clamp 102, a pin clamp 104, and a base assembly or saddle assembly 106 disposed therebetween. Each clamp 102, 104 independently receives and secures a bar, pin or other fixation element. Other embodiments of the clamping device 100 include two bar clamps or two pin clamps. Yet other embodiments include only a single clamp on one end, with a multi-clamp set or other arrangement on the other end.

Figure 2:
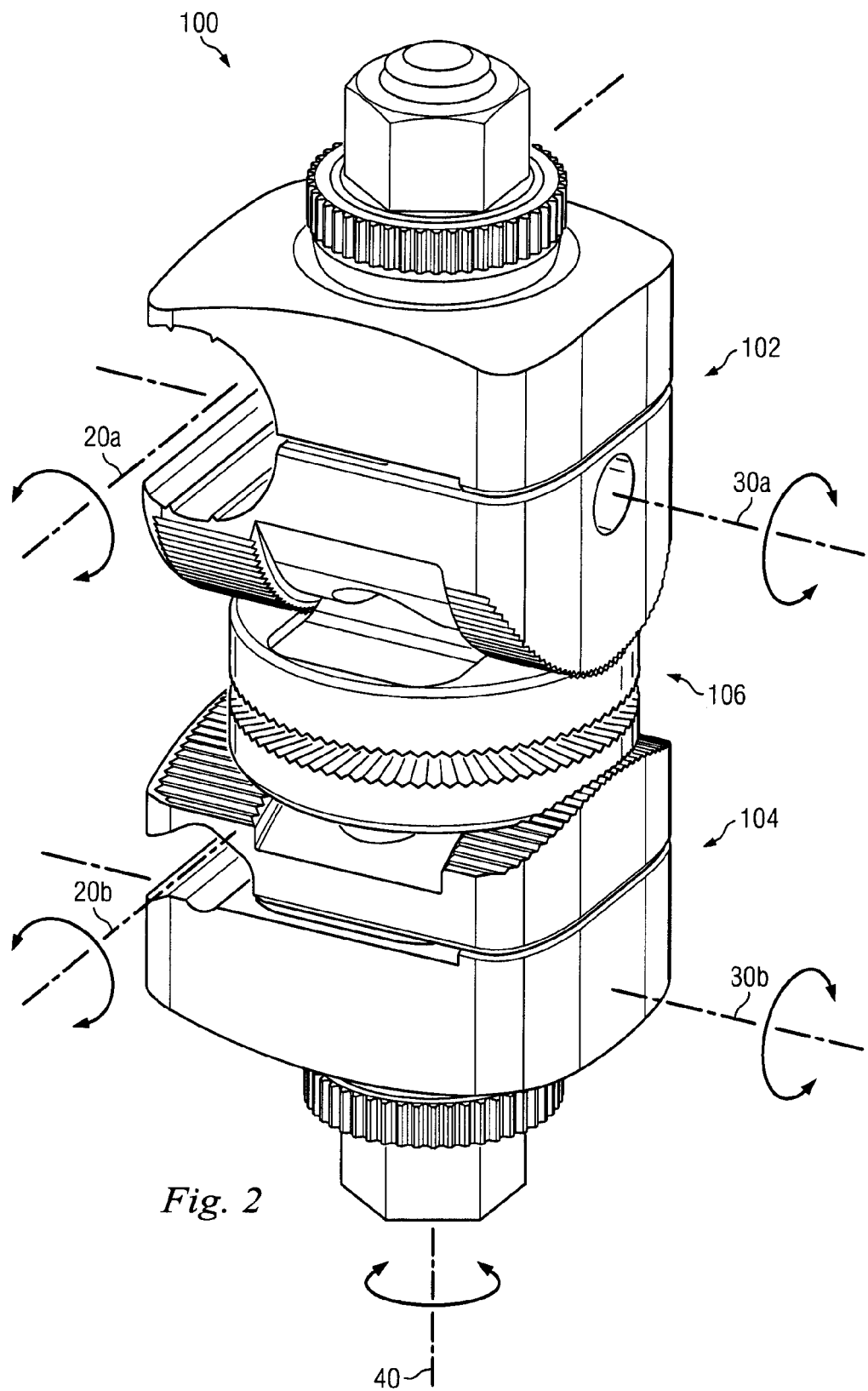
FIG. 2 is an illustration of a clamping device from the external fixation system of FIG. 1 in accordance with one exemplary aspect of the present disclosure.

Each clamp 102, 104 of the clamping device 100 provides multiple degrees of freedom. FIG. 2 shows the degrees of freedom as a roll axis 20, a pitch axis 30, and a yaw axis 40 in the upper and lower clamps 102, 104. The roll axis 20 is the axis of a fixation element within the clamps and about which the clamping device 100 may rotate when the clamp is only provisionally locked. The pitch axis 30 is the axis about which the outer and inner jaws rotate relative to the saddle assembly 106 and relative to the opposing clamp. The yaw axis 40 is defined by a stud (described below) and about which one of the clamps 102, 104 can rotate relative to the other.

Figure 3:
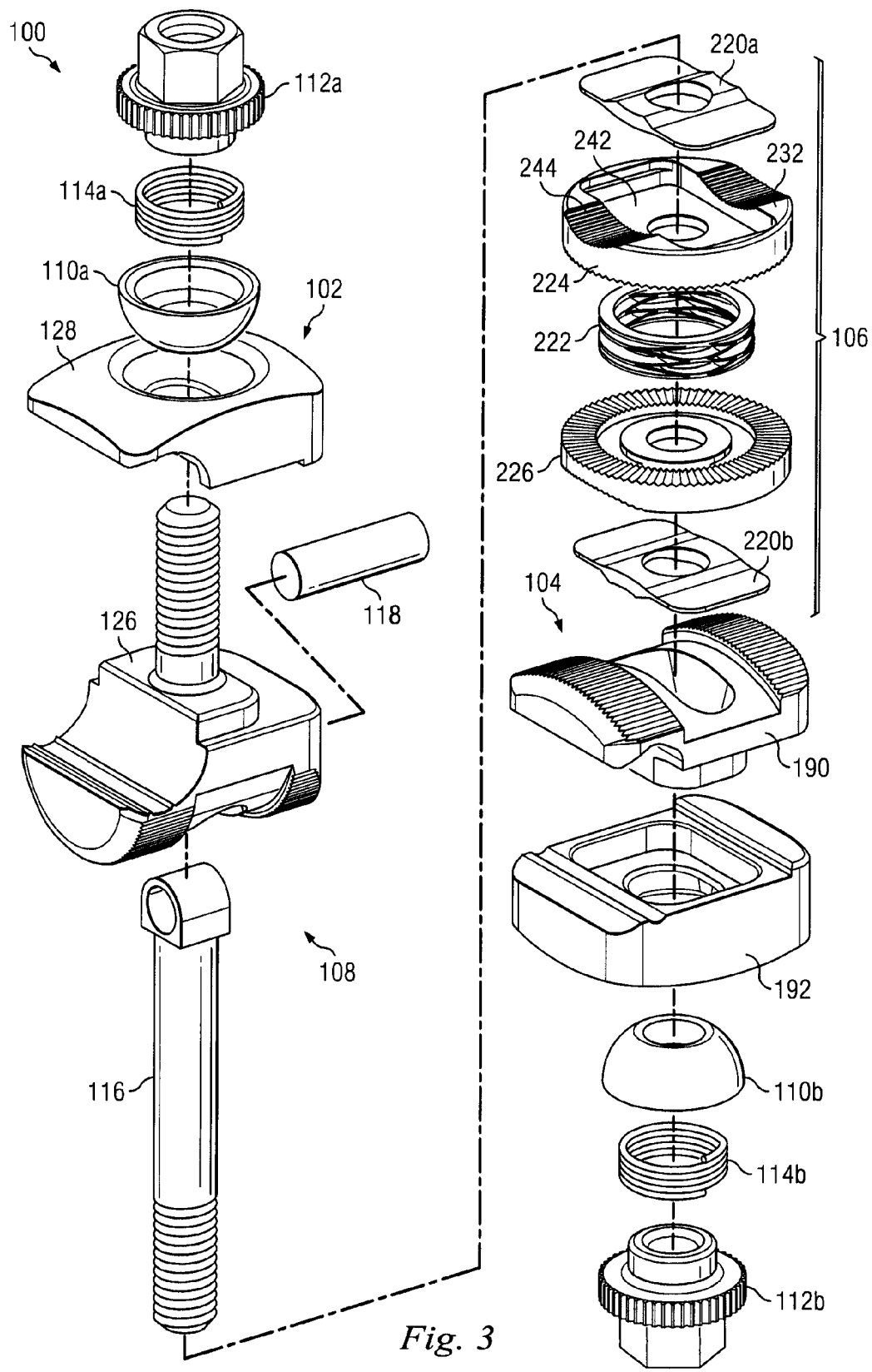
FIG. 3 is an illustration of an exploded view of the clamping device of FIG. 2.
Figure 4:
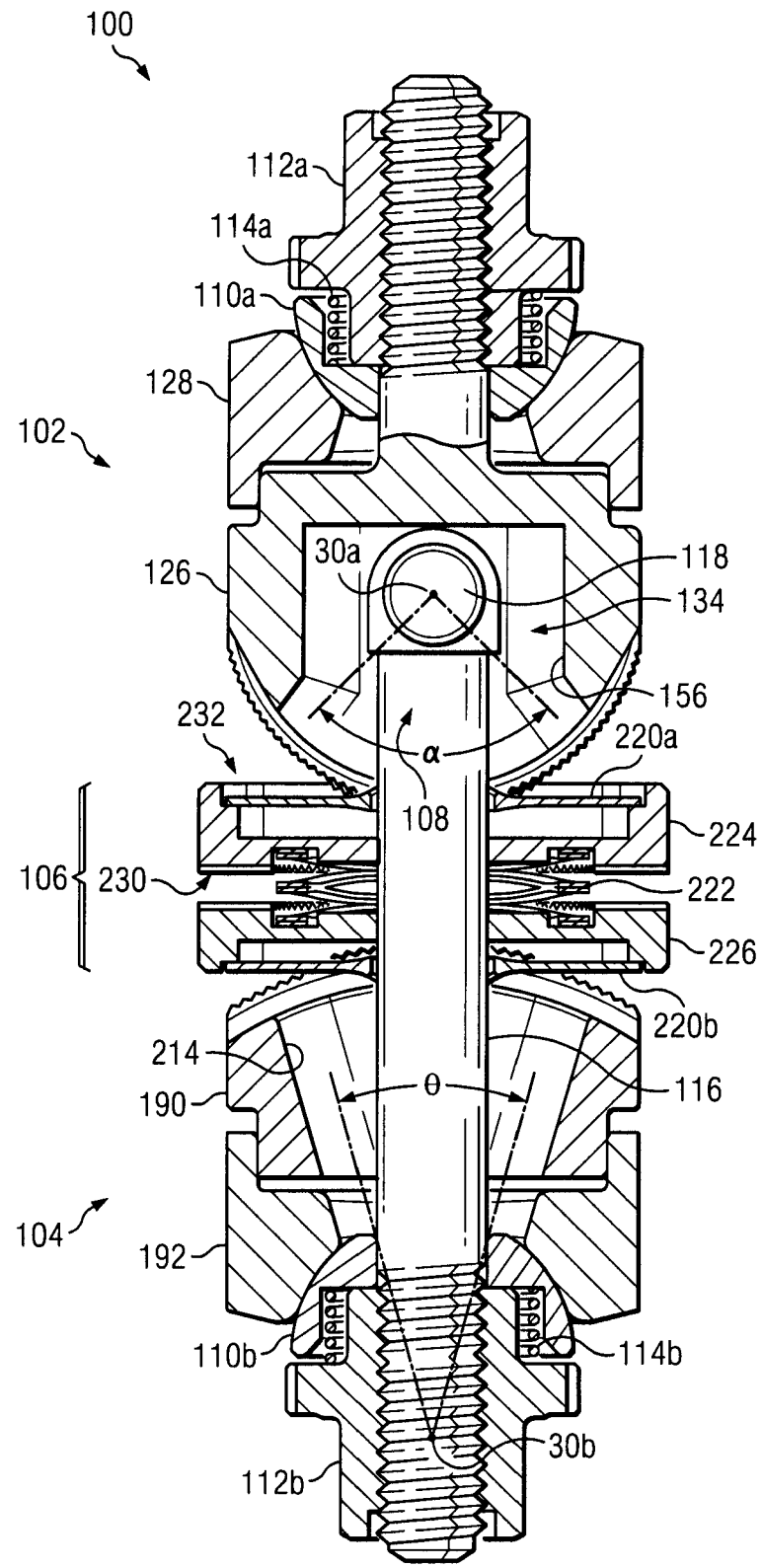
FIG. 4 is an illustration of a cross-sectional view of the clamping device of FIG. 2.
Figure 5:
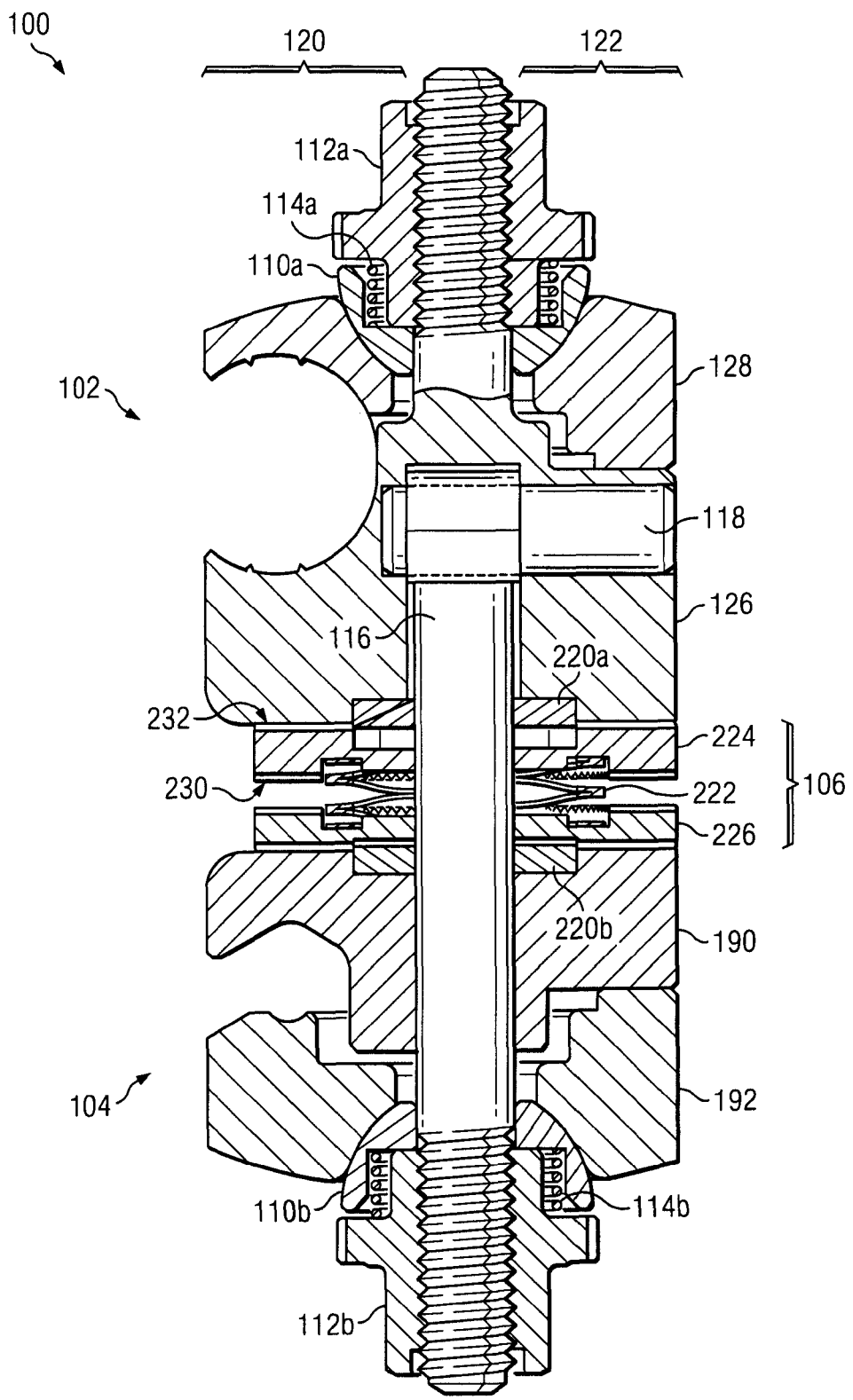
FIG. 5 is an illustration of a cross-sectional view of the clamping device of FIG. 2 taken transverse to the cross-sectional view in FIG. 4.

FIGS. 2 and 3 respectively show an isometric view and a partially exploded view of the clamping device 100, while FIGS. 4 and 5 show cross-sectional views. Referring to FIGS. 2-5, in addition to the clamps 102, 104 and saddle assembly 106, the clamping device 100 includes a swivel element 108, spherical washers 110, and nuts 112. Biasing springs 114 are disposed between the spherical washers 110 and the nuts 112. The swivel element 108 includes a stud 116 and an axle 118. The stud 116 extends through a portion of the device 100 and divides the device into a clamping side 120 representing the side of the device where fixation elements are held and introduced, and a rearward side 122 representing the side of the device opposite the clamping side.

The clamps 102, 104 each include an inner jaw and an outer jaw. The bar clamp 102 will be described first. The bar clamp 102 includes an inner jaw 126 and an outer jaw 128 that define an opening for reception of a fixation element. These cooperate with the spherical washer 110 and the biasing element 114 to apply loading that clamps the fixation element between the inner and outer jaws.

Figure 6A:
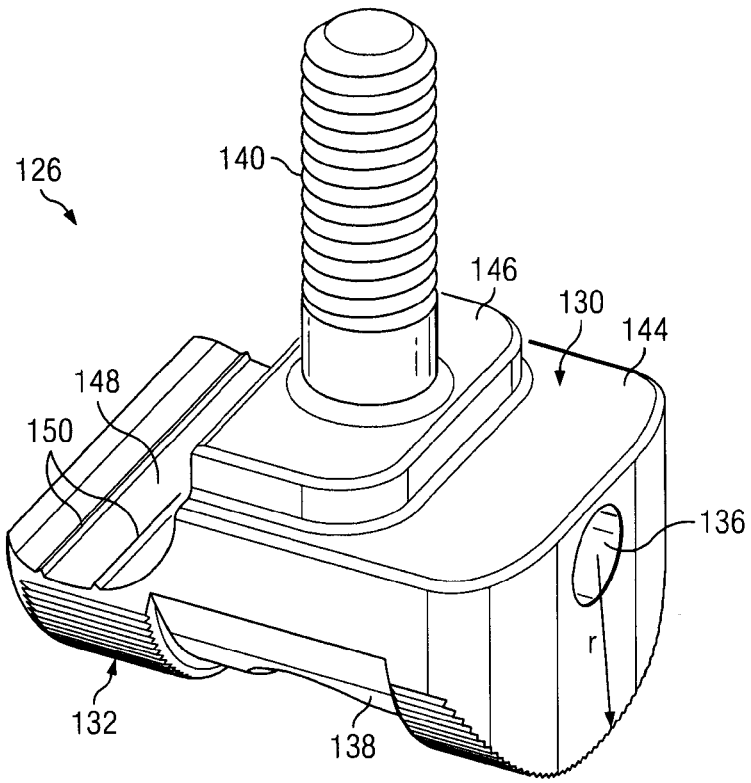
FIGS. 6A-6C are illustrations of an exemplary inner jaw of the clamping device in FIG. 2 in accordance with one exemplary aspect of the present disclosure.
Figure 6B:
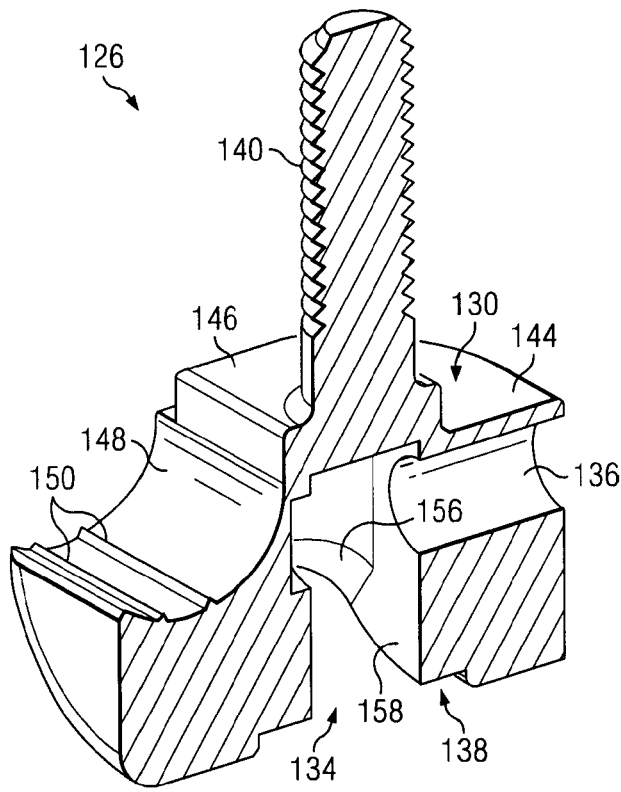
Figure 6C:
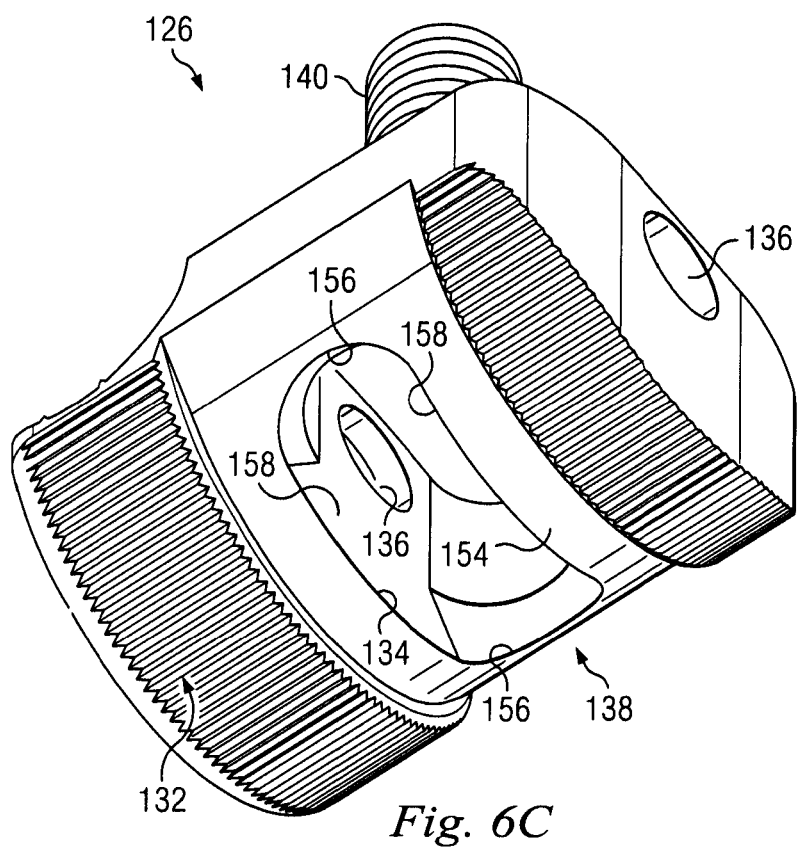

FIGS. 6A-6C show views of the inner jaw 126. FIG. 6A is an isometric view and FIG. 6B is a cross-sectional view. FIG. 6C shows the surface that interfaces with the saddle assembly 106. The inner jaw 126 cooperates with the outer jaw 128 to clamp onto and secure a fixation element. The inner jaw 126 includes an inner clamp face 130 that faces toward the outer jaw 128 and an outer clamp face 132 that interfaces with the saddle assembly 106. It also includes a central bore 134, a transverse bore 136, a saddle assembly receiving area 138, and a tightening post 140.

The inner clamp face 130 includes a body surface portion 144, an alignment portion 146, and a fixation element gripping surface portion 148. In the example shown, each of the body surface portion 144, the alignment portion 146, and the gripping surface portion 148 are vertically offset. The body surface portion 144 is disposed generally toward the rearward side 122 (FIG. 5) of the clamping device 100 and the gripping surface portion 148 is disposed at the clamping side 120 (FIG. 5) of the clamping device 100.

The alignment portion 146 is a non-circular boss extending from the body surface portion 144 and configured to be received into a receiving portion on the outer jaw 128. Its non-circular perimeter corresponds with the shape of the receiving portion on the outer jaw 128 to limit relative rotation of the inner and outer jaws as can be seen in the cross-sectional views.

The gripping surface portion 148 is configured to interface with a fixation element such as a rod 12 from FIG. 1. In this example, the gripping surface portion 148 is a lateral recess that includes a plurality of transverse teeth 150 formed therein. The plurality of transverse teeth 150 extend from one lateral side to the other and are configured to interface or engage with a fixation element that is held between the inner and outer jaws 126, 128. Other embodiments of the gripping surface portion 148 include other gripping features, while still others include a smooth surface.

The outer clamp face 132 is a semi-cylindrical shaped surface that includes parallel, longitudinal splines shown in FIGS. 6A and 6C. These are configured to interdigitate with the corresponding splines on the saddle assembly 106, as shown in FIGS. 2-5. The cylindrical shaped surface defines a radius r about which the inner jaw 126 pivots to provide the range of motion. Naturally, pivoting only occurs when the inner jaw 126 and the saddle assembly 106 are spaced so that the splines are not engaged. In some examples, in place of the splines, the inner jaw 126 includes knurling, a roughened surface or other friction inducing features are used to enable the inner jaw 126 and the saddle assembly to be selectively secured relative to each other. The outer clamp face 132 is shaped to define the pitch axis 30 described above.

The saddle receiving area 138 is a gap formed into the outer clamp face 132. It includes a recessed articulating surface 154 that is semi-cylindrical and concentric with the outer clamp face 132. The area 138 is shaped to receive a portion of the saddle assembly 106, and the articulating surface 154 engages and articulates with the saddle assembly 106. As such, unlike the outer clamp face 132, the articulating surface 154 is configured to provide smooth rotation about the pitch axis 30.

As best seen in FIG. 6C, the central bore 134 is a transversely extending slot-like opening having a generally rectangular shape with a width and a length and the length being longer than the width. In the embodiment shown, the central bore 134 has rounded or arching ends 156 separated by substantially parallel side edges spaced by the width. As best seen in FIGS. 6B and 6C and in the cross-sectional view of FIG. 4, the ends 156 of the central bore 134 having a cylindrical portion and a conical-shaped portion such that the bore length increases as the bore depth approaches the outer clamp face 132. In contrast, bore sidewalls 158 are substantially parallel to each other, maintaining the bore width substantially constant.

The transverse bore 136 extends, in this embodiment, from an outer, rearward side of the inner jaw 126 to the central bore 134, and into the opposing sidewall of the central bore 134. This transverse bore 136, as will be discussed below, receives the axle 118 and serves as an axle seat.

The stud 116 fits within the central bore 128 as shown in FIGS. 4 and 5. The shape of the central bore 136 permits only very limited movement relative to the stud 116 in the width direction. However, because the bore length is greater than the bore width, the inner jaw 126 may move relative to the stud 108 substantially more in the transverse, or length direction about the pitch axis 30, to change the pitch of the inner jaw 126 relative to the stud 116.

This ultimately changes the pitch of the inner jaw 126 relative to the saddle assembly 106. In the embodiment shown, the inner jaw 126 pivots relative to the saddle assembly about 35 degrees in each direction, giving a pivot range of about 70 degrees. However, it should be apparent that in other embodiments, the pivot range may be higher or lower than this amount. For example, some embodiments have a pivot range of about 50 degrees or greater. In other embodiments, the pivot range is about 90 degrees or greater. In other examples, the pivot range is about 120 degrees or greater, and in one embodiment, 150 degrees or greater. Other ranges are contemplated. The pivot range may be affected by the diameter of the stud 108, the length of the central bore 134, as well as the angle of the rounded bore ends 156.

Known systems had limited pivot ranges about the pitch axis because the clamp pivoted relative to the stud, and the stud was used to provide a clamping load onto the clamp. As such, the clamping load was reduced to the cosine of the pitch angle, requiring designers to limit the amount of angulation. However, the embodiment disclosed herein permits the clamping load to pitch with the clamp set, permitting the angulation to increase substantially. Separating the clamping load direction from the pitch angle means that designers can design the clamp to pitch to any desired pitching range.

These advantages are obtained by the use of the tightening post 140, that is independent of the stud 116. In this example, the tightening post 140 extends from the inner clamp face 130 toward and through the outer jaw 128. Here, it extends normal to the inner clamp face 130. The tightening post 140 is sized to extend through the outer jaw 128 and is configured to cooperate with the tightening nut 112 to apply the tightening load on the fixation element. As such, the tightening force is normal to the jaws' clamp surfaces at all times.

Figure 7A:
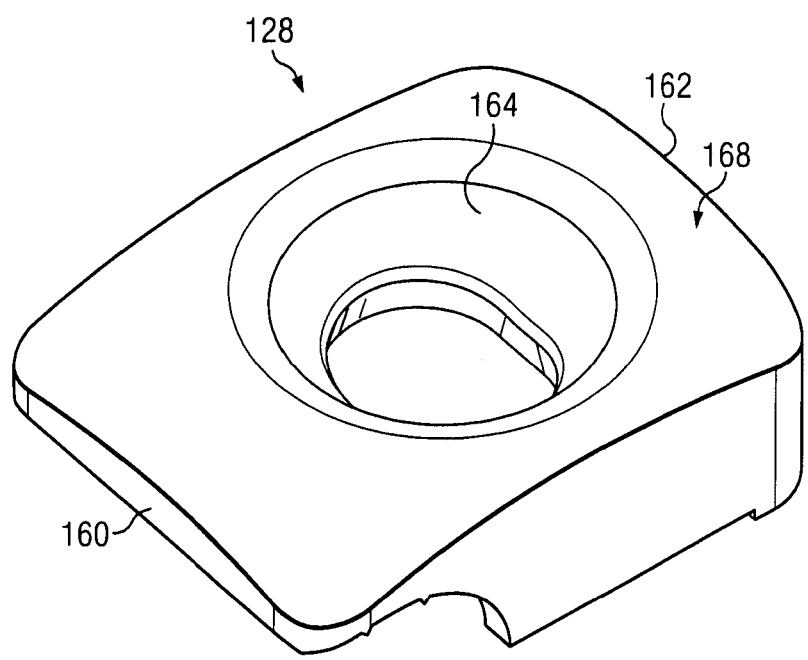
FIGS. 7A and 7B are illustrations of an exemplary outer jaw of the clamping device in FIG. 2 in accordance with one exemplary aspect of the present disclosure.
Figure 7B:
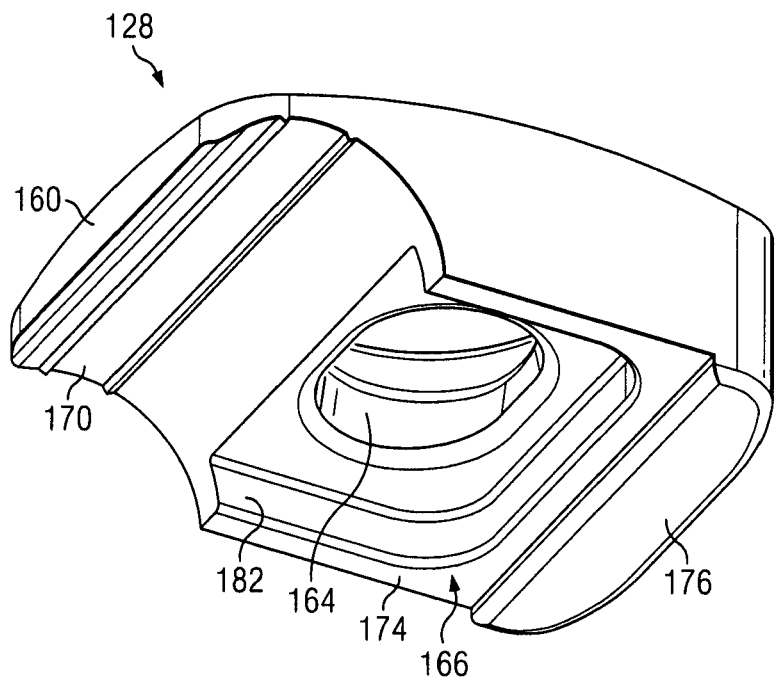
Figure 8A:
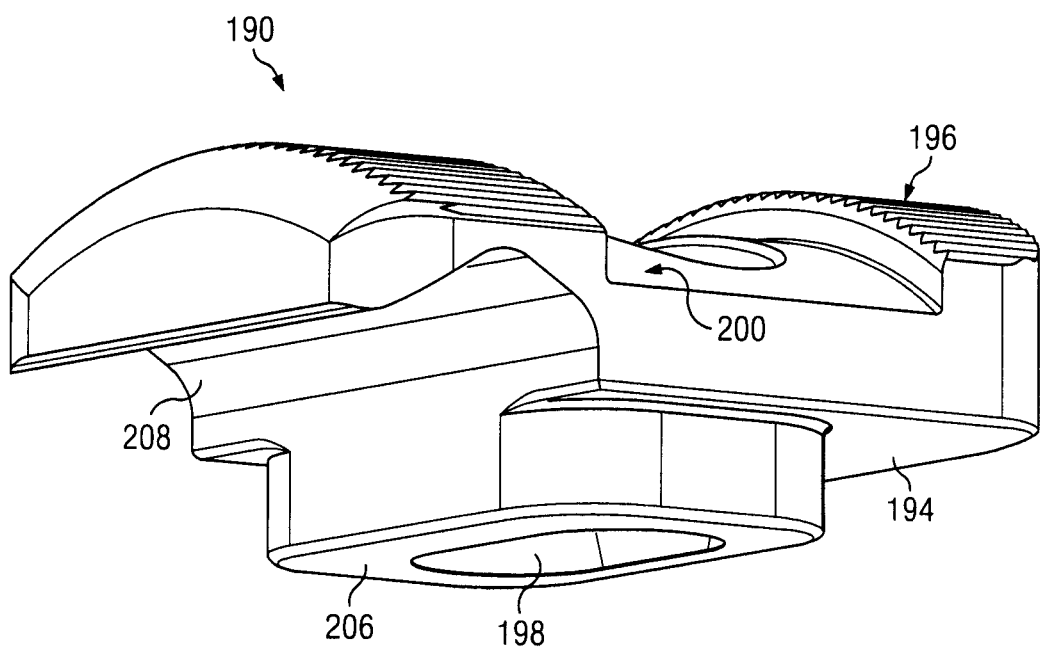
FIGS. 8A and 8B are illustrations of another exemplary inner jaw of the clamping device in FIG. 2 in accordance with one exemplary aspect of the present disclosure.
Figure 8B:
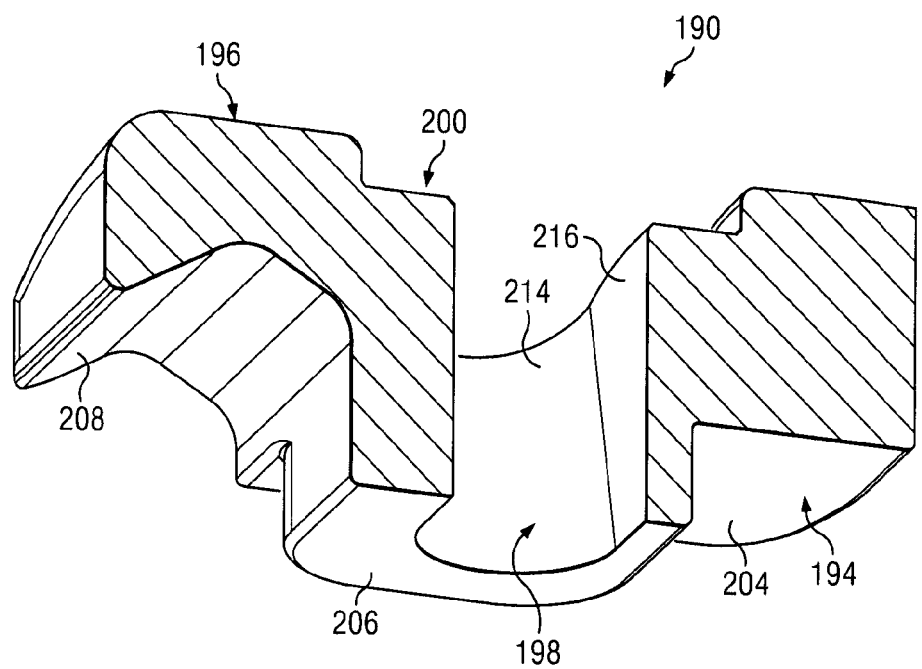

FIGS. 7A and 7B show the outer jaw 128 in greater detail. The outer jaw 128 includes a front end 160, a rearward end 162, a central bore 164, an inner clamp face 166, and an outer clamp face 168. The inner clamp face 166 includes a fixation element-receiving gripping surface portion 170 formed as a transverse groove adjacent the front end 160. The gripping surface portion 170 extends from one lateral side to another and is shaped to cooperate with the inner jaw 126 to receive and secure a bar, pin or other fixation element in place between the inner and outer jaws. As shown in the cross-section of FIG. 5, the gripping surface portion 170 aligns with the gripping surface portion 148 on the inner jaw 126 to define an opening and a passage that captures a fixation element therein. The gripping surface portion 170 may be formed with a rounded bottom portion, flats, faces, or some combination of both.

The central bore 164 includes features that enable it to articulate relative to the tightening post 140 and about the spherical washer 110. At the inner clamp face 166, the central bore 160 is relatively oval shaped, with curved ends connected by parallel sides. At the outer clamp face 168, the central bore 164 is formed with a round spherical portion shaped to receive the spherical washer 110.

The inner clamp face 166 of the outer jaw 128 includes a body surface portion 174, a leveraging step 176, and the gripping surface portion 170. The body surface portion 174 includes an alignment recess 182 that is shaped to receive the alignment portion 146 on the inner jaw 126. Because of the non-circular shape, relative rotation between the inner and outer jaws 126, 128 is limited. The leveraging step 176 is disposed toward the rear side of the outer jaw 128 and located to interface with the body surface portion 144 of the inner jaw 126. When the locking nut 112 is tightened, the outer jaw 128 is sized and configured to contact the inner jaw 126 with the leveraging step 176 and also to contact the fixation member between the jaws. Accordingly, these two regions of contact enable the clamp to positively lock onto and apply loading directly onto the fixation element.

The pin clamp 104 includes an inner jaw 190 and an outer jaw 192 and is described with reference to FIGS. 3-5, 8A, and 8B. These inner and outer jaws 190, 192 include many of the features of the inner and outer jaws 126, 128 of the bar clamp 102 discussed above and will not be repeated here. The inner and outer jaws 190, 192 are configured however to clamp on a pin fixation element, and therefore includes fixation element-receiving surfaces shaped in a manner to receive the pins, which often have a diameters smaller than that of the rods. The outer jaw 192 will not be described further here, but may include pin gripping surface portions similar to those of the rod, for example, like those describe in the incorporated documents, or otherwise. The inner jaw 190 is shown in detail in FIGS. 8A and 8B. It includes an inner clamp face 194 that faces toward the outer jaw 192 and an outer clamp face 196 that interfaces with the saddle assembly 106. It also includes a central bore 198 and a saddle assembly receiving area 200.

The inner clamp face 194 includes a body surface portion 204, an alignment portion 206, and a fixation element gripping surface portion 208. In the example shown, each of the body surface portion 204, the alignment portion 206, and the gripping surface portion 208 are vertically offset. The body surface portion 204 is disposed generally toward the rearward side 122 (FIG. 5) of the clamping device 100 and the gripping surface portion 208 is disposed at the clamping side 120 (FIG. 5) of the clamping device 100.

The alignment portion 206 is similar to the alignment portion 146 discussed above and will not be further discussed. The gripping surface portion 208 is configured to interface with a fixation element such as a pin 14 from FIG. 1. In this example, the gripping surface portion 208 is formed as a transverse recess. Other embodiments of the gripping surface portion 208 include teeth, flats, or other shaped fixation element engaging surfaces. The outer clamp face 196 is similar to that of the inner jaw 126 described above, with a different radius, as explained further below. The outer clamp face 196 is shaped to define the pitch axis 130b described above.

The saddle receiving area 200 is a gap formed into the outer clamp face 196 in the manner described above. In this instance however, the central bore 198 extends through the inner jaw from the inner clamp face 194 to the outer clamp face 196. According, instead of having a tightening post as does the inner clamp 126, the inner clamp 190 is configured so that the stud 116 passes entirely through. The central bore 198 is shown in cross-section in FIG. 8B, and also in FIGS. 4 and 5. The central bore 198 is a transverse opening having a generally rectangular shape with a width and a length and the length and rounded or arching ends 214 separated by substantially parallel side edges 216 spaced by the width. The ends 214 of the central bore 198 form a conical-shaped portion such that the bore length increases as the bore depth approaches the outer clamp face 196. In contrast, bore sidewalls 216 are substantially parallel to each other, maintaining the bore width substantially constant.

The stud 116 passes entirely through the central bore 198 as shown in FIGS. 4 and 5. The inner jaw 190 may move relative to the stud 116 about the pitch axis 30 to change the pitch of the inner jaw 190 relative to the stud 116.

The pin clamp 104 is locked onto a fixation element by tightening the locking nut 112b onto the stud 116. However, when the clamp 104 is angled, the locking force on the fixation element is reduced as described above, with the greater the angle, the greater the reduction. Therefore, the pitch angle may be limited to ensure a sufficient locking load is directed on the fixation element.

As shown in FIGS. 3-5, the base assembly saddle assembly 106 includes biasing elements as leaf springs 220, a biasing element as a helical wire spring 222, and a first base component or saddle 224 that associates with the bar clamp 102, and a second base component or saddle 226 that associates with the pin clamp 104. The saddle assembly 106 is arranged to permit the bar clamp 102 to rotate relative to the pin clamp 104 when the clamping device 100 is in an unlocked condition. In addition, the saddle assembly 106 provides a foundation or base for each of the bar clamp 102 and the pin clamp 104 to each independently pivot about their respective pitch axes 130 in FIG. 2. FIGS. 4 and 5 show a cross-section of the saddle assembly 106.

Figure 9:
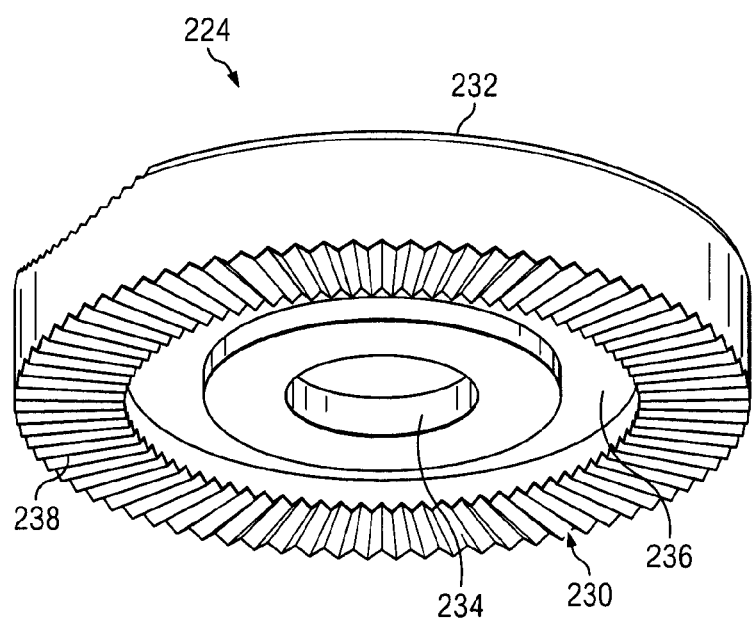
FIG. 9 is an illustration of a base component or saddle of the clamping device in FIG. 2 in accordance with one exemplary aspect of the present disclosure.

FIG. 9 shows the saddle 224 in greater detail. The saddle 226 includes the same features, but has a different dimension matching it to the pin clamp as will be discussed below. Referring to FIG. 9, the saddle 224 includes an inner facing side 230 and an outer facing side 232. FIGS. 3 and 4 show the inner facing side of the saddle 224 facing the opposing second saddle 226, while the outer facing side 232 is arranged to face the adjacent inner jaw 126 of the bar clamp 102. The saddle 224 includes a centrally disposed through hole 234, a bias member seat or spring seat 236, and a saddle interfacing portion 238 with radial interdigitations. The through hole 234 is sized and configured to receive the stud 116 and is sized to permit the saddle 224 to freely rotate about the stud 116. The saddle interfacing portion 238 is disposed between the spring seat 276 and the saddle perimeter and is configured to selectively engage with and provide positive retention from planar rotation when the faces are clamped together, thereby preventing relative rotation between the first and second saddles 224, 226 when the clamping device 100 is in a fully locked condition or, when used with embodiments without an opposing clamp, that selectively engage with and prevent relative rotation with some other foundation.

The wire spring 222 is disposed between and biases the saddles 224, 226 apart so that they can freely rotate except when the saddle assembly is locked. When placed in a locked condition, the wire spring 222 compresses within the spring seat 236 and the opposing radial interdigitations engage, preventing further relative rotation.

The outer facing side 232 includes a bias member seat or leaf spring seat 242 and a clamp interfacing portion 244, best seen in FIG. 3. The leaf spring seat 424 receives the leaf spring 220 that is in contact with the saddle assembly receiving area 138 and biases the outer clamp surface 132 with its splines away from the splines in the saddle's clamp interfacing portion 244. Accordingly, when in a un-tightened or unlocked state, the clamps can pivot about the pitch axis relative to the saddle assembly 106. However, when the nut 112b is tightened, the inner jaws are forced toward the saddles, the leaf springs 220 deflect, and the splines on the inner jaws engage the splines on the saddle and prevent further displacement along the pitch angle. The leaf spring seat 242 may include shelves on which ends of the leaf spring 220 can rest. In this way, the leaf springs 220 can be secured within the leaf spring seat 242, but also deflect inwardly. The leaf springs 220 may also aid in maintaining alignment of the inner jaws and the saddles. Although shown here with leaf springs and wire springs, other biasing elements may be used, including washer springs and other springs.

As described above, the swivel element 108 includes the stud 116 and the axle 118. The stud includes a distal end and a proximal end with a transverse through hole at the distal end and threads on the proximal end. The distal end of the stud 116 is disposed within the central bore 134 of the inner jaw 126, and the stud 118 extends through the saddle assembly 106 and through the pin clamp 104. However, in this embodiment, the stud 116 does not extend through the top of the inner jaw 126 or through the outer jaw 128. The stud 116 is maintained within the inner jaw 126 by the axle 118. As can be seen in FIGS. 4 and 5, the axle 118 extends through the transverse bore 136 in the inner clamp 126, through the transverse bore at the distal end of the stud 116, and is lodged into the opposing sidewall of the central bore 134. Accordingly, the transverse bore 136 is an axle seat that secures the axle 118 in place, which fixes the stud 116 in place. In this example the stud hole and the axle are sized to provide smooth rotation of the stud 116 about the axle 118. The axle 118 is sized to be press fit into the transverse bore 136. In other examples however, the axle 118 may be pinned or otherwise contained within the transverse bore 136. In one example, the axle 118 is press fit into the stud 116 and has a sliding fit with the transverse bore 136. In a further example, the stud and axle are formed as a single component such as a monolith. The axle is concentric with the pitch axis 30a in FIG. 1.

The cross-sectional view in FIG. 4 shows the pivot range α of the bar clamp 102 and the pivot range θ of the pin clamp 104. The outer clamp face 132, 196 of each of the inner jaws 126, 190 defines the respective pitch axis 30a, 30b about which the clamps 102, 104 can pivot relative to the stud 118. As can be seen, the pitch axis 30a defined by the outer clamp face 132 corresponds to the axis of the axle 118. Likewise, the pitch axis 30b is defined by the cylindrical outer clamp face 196 of the jaw 190. The dashed lines in FIG. 4 represent the rotation limits based on the diameter size of the shaft and the end walls of the central bores 134, 198 of the respective inner jaws 126, 190.

As can be seen, the pitch range or pivot range α in the bar clamp 102 is about 70 degrees, and the pitch range or the pivot range θ of the pin clamp 104 is about 40 degrees. It should be apparent that in other embodiments, the pivot range may be higher or lower than this amount. For example, some embodiments of the rod clamp 102 have a pivot range α of about 50 degrees or greater. In other embodiments, the pivot range α may be about 90 degrees or greater. In other examples, the pivot range α may be about 120 degrees or greater, and in one embodiment, 150 degrees or greater. Other ranges are contemplated. The pivot range may be affected by the diameter of the stud 108, the length of the central bore 134, as well as the angle of the rounded bore ends 156. In this instance, the pivot range θ of the pin clamp is limited in order to ensure that the locking force is sufficient to secure the fixation element within the clamp 104. However, the bar clamp 102 is able to pivot much further since the locking force will always act directly transverse to the fixation clamp.

In use, a surgeon may place the clamping device 100 in the open position by loosening the locking nuts 112 at both the bar clamp end and the pin clamp end. In this condition the helical wire spring 222 biases the saddles 224, 226 apart, and the leaf springs 220 bias the inner jaws and the saddles apart. As such, all interfaces are loose and can be manipulated.

The surgeon may then introduce a fixation element into each of the rod and pin clamps. With the fixation element captured between the jaws, the clamping device 100 is in a provisionally locked condition. That is, the fixation element is provisionally secured within the clamp between the outer and inner jaws. In this position, the fixation element may be rotated within the clamp, the complete clamping device may be rotated about the fixation element, the clamp may be slid along the fixation element, and the inner and outer jaws 116, 118 may be pivoted relative to the saddle assembly 106 and rotated about the stud 108. Thus, the clamp captures a fixation element but permits continued adjustment as the surgeon finishes locating the pins or building the frame. As discussed above, this may include manipulating the bar clamp 102 about the pitch axis 30a over a large pivot range. In one example, the bar clamp may pivot over a maximum pivot range within about the range of 50 and 180 degrees. In other embodiments, the pivot range is between 50 and 120 degrees. In other example, the pivot range is within 75 and 120 degrees, and in yet other examples, the pivot range is about 90 degrees. Other ranges are contemplated. Because of the axle connection, the post pivots relative to the bar clamp 102 within a single plane.

Once the pins and bars are in a desired position, and with reference to FIG. 4, the surgeon locks the clamping device 100 against further movement. Tightening the nut 112a on the bar clamp 102 locks the fixation element in place in the bar clamp 102. The surgeon then locks the pin clamp 104 by tightening the nut 112b. This draws the inner jaw 126 of the bar clamp 102 toward the locking nut 112b. As the nut is tightened, the wire spring 222 compresses, and the interdigitations on the saddles provide positive retention from relative planar rotation. In addition, the leaf springs 220 separating the saddles 224, 226 and the inner jaws deflect, so that the splines on the inner jaws engage the splines on the concave side of the saddles 224, 226, and the spherical washer 110b tightens against the outer jaw 192. The outer jaw 192 then is forced against the fixation element to more tightly secure the fixation element in place between the jaws. Thus, in a fully locked state, the clamping device 100 is locked against all relative movement of the clamps, including releasing the fixation element.

To release the bar, the surgeon performs the steps in reverse. Particularly, he first loosens both of the nuts 112, placing the clamping device 100 in the provisionally locked state. Then he may grasp and pull the fixation elements out from between the jaws of the clamps.

As is apparent by a review of the drawings, the pitch axis created by the geometry of the saddle 226 and the inner jaw 190 in the above embodiment is a redundant degree of freedom. However, in one embodiment, the bottom side of the inner jaw 190 has the geometry of the saddle 226, eliminating the need for the second leaf spring and simplifying the overall construct of the clamping device 100. It is contemplated that other jaw sets may incorporate this feature, such as one piece jaw sets or jaw sets that incorporate latching features.

It is worth noting that the clamp embodiments disclosed herein may be substituted with alternative clamps, including clamps having a separate latch component. One example of these types of clamp is shown and described in incorporated U.S. patent application Ser. No. 13/175,343, titled Multi-Locking External Fixation Clamp, filed Jul. 1, 2011. Those clamps may be substituted for the clamps disclosed herein, as modified if necessary to cooperate with a swivel element, such as the swivel element 108.

FIGS. 10-13, 14A, and 14B show another embodiment of a clamping device, referenced here by the numeral 400. This clamping device 400 is configured much like the clamping device 100 discussed above, and includes a bar clamp 402, a multi-pin clamp 404, and a saddle assembly 406. Much of the discussion above apples equally to the clamping device 400, and will not be repeated in detail here. Fixation elements shown as a bar 12 and pins 14 are held in the clamping device 400.

Figure 10:
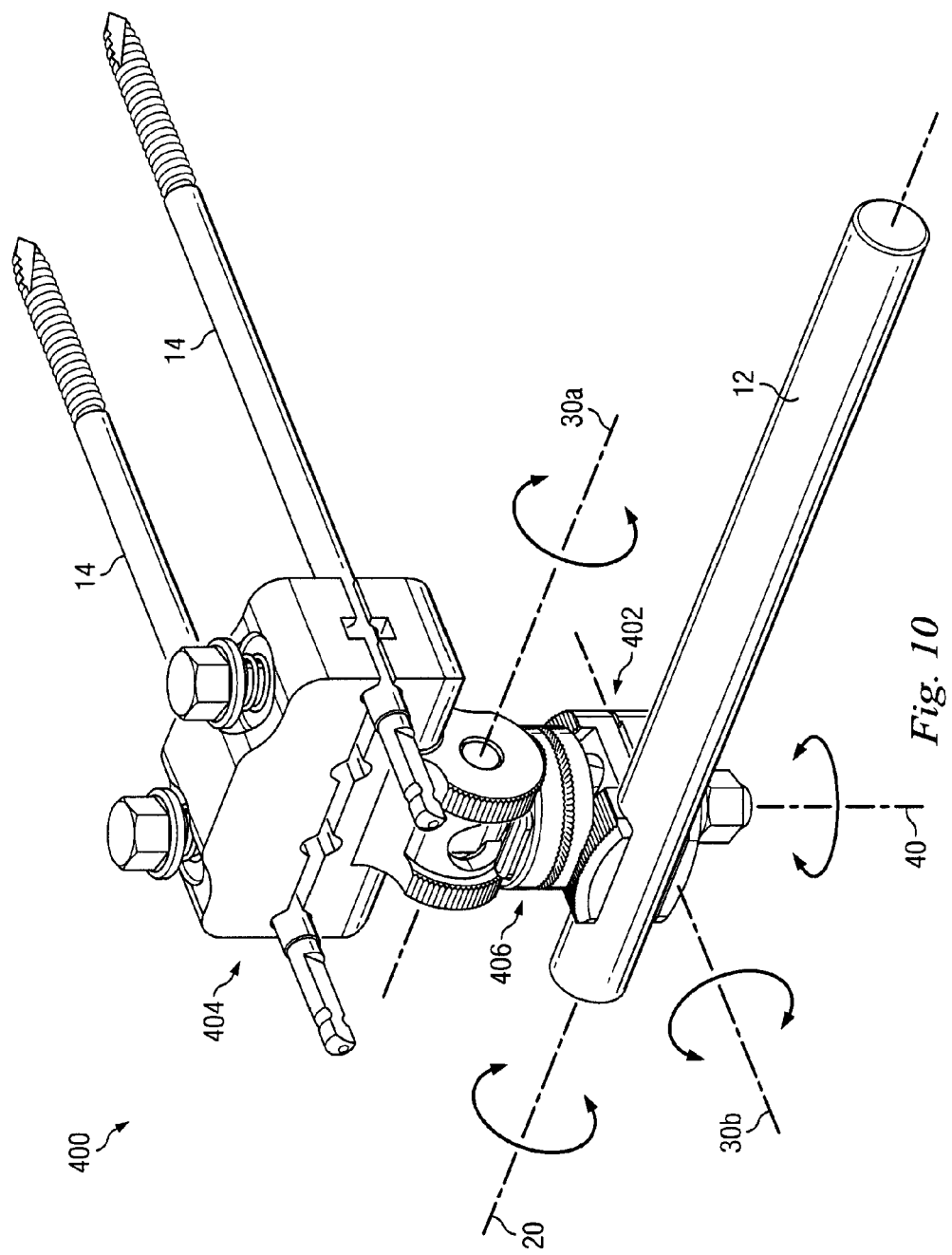
FIG. 10 is an illustration of another exemplary external fixation system in accordance with one exemplary aspect of the present disclosure.

The clamping device 100 provides multiple degrees of freedom. FIG. 10 shows the degrees of freedom as a roll axis 20, a pitch axis 30, and a yaw axis 40. In the example shown the pin clamp 104 also includes a pitch axis 30*a*, shown with the clamp disposed so that the pins 14 are transverse to the rod 12.

Figure 11:
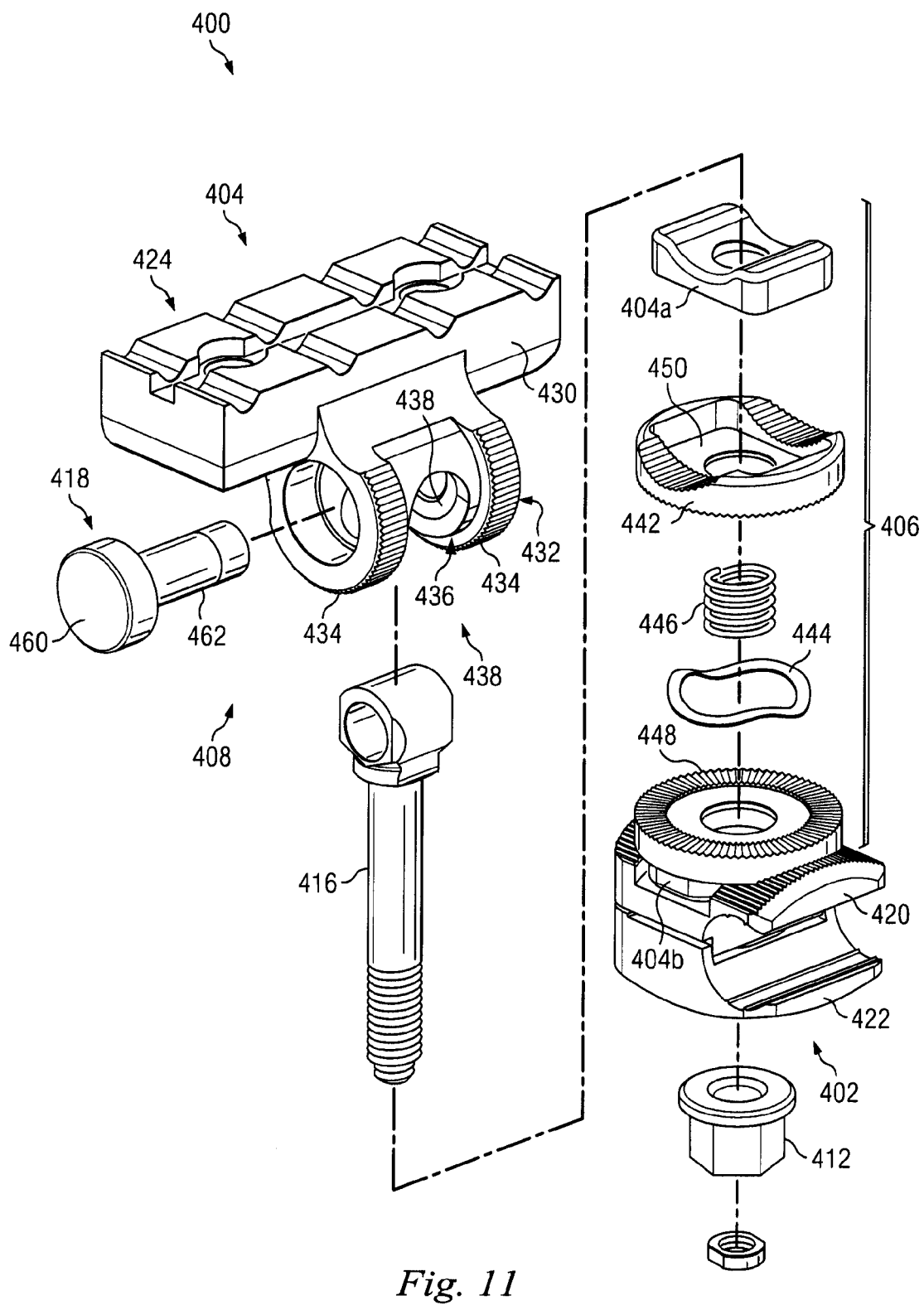
FIG. 11 is an illustration of a partially exploded view of the clamping device of FIG. 10.
Figure 12:
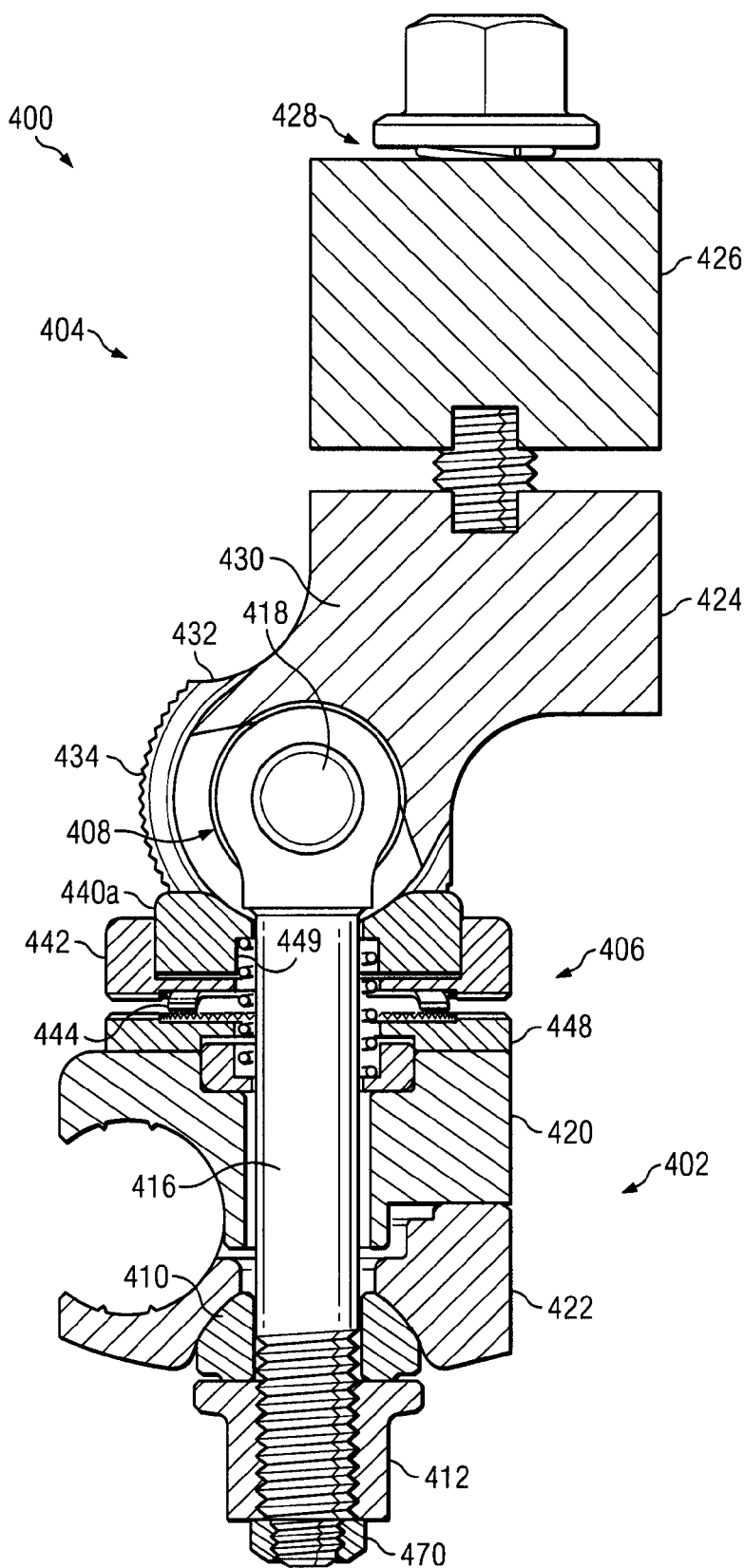
FIG. 12 is an illustration of a cross-sectional view of the clamping device of FIG. 10.
Figure 13:
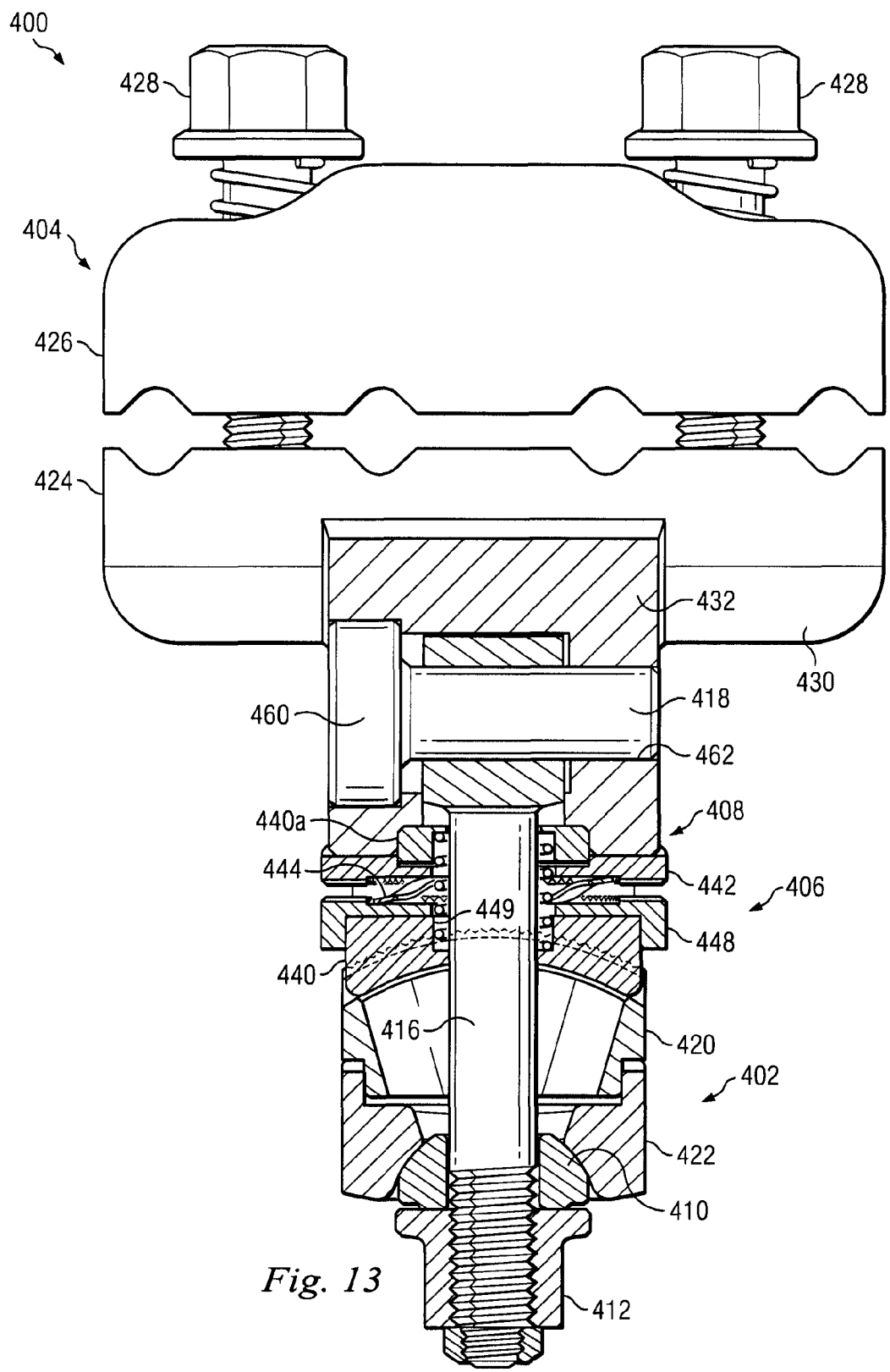
FIG. 13 is an illustration of a cross-sectional view of the clamping device of FIG. 10 taken transverse to the cross-sectional view in FIG. 12.

FIGS. 11-13 respectively show a partially exploded view of a portion of the clamping device 400, a cross-sectional view, and a cross-sectional view taken transverse to the cross-sectional view in FIG. 12. Referring to FIGS. 11-13, in addition to the clamps 402, 404 and saddle assembly 406, the clamping device 400 includes a swivel element 408, a spherical washer 410, and a locking nut 412. The swivel element 408 includes a stud 416 an axle 418.

The bar clamp 402 will be describe first. This clamp 402 includes an inner jaw 420 and an outer jaw 422. In this example, these jaws correspond to the jaws of the pin clamp 104 described above, but are shaped to receive and capture a fixation rod. These will not be described further here. In this example however, the coil spring 114 has been removed and its action has been replaced with a component of the saddle assembly, which will be described below.

The pin clamp 404 includes an inner jaw 424 and an outer jaw 426. These jaws are multi-pin clamp jaws clampable upon fixation elements using two locking components 428. In this example, the locking component are bolts and springs, with the springs biasing the outer jaw 426 toward the inner jaw 424 in a manner that provisionally secures fixation elements between the jaws until they are locked in place by tightening the bolts. The clamping portion of these jaws are similar to those described in a co-pending application titled Single Lock External Fixation Clamp Arrangement and Method, application Ser. No. 13/271,744 filed on Oct. 12, 2011,the same day as the present disclosure, incorporated herein by reference.

The inner jaw 424 however includes a main body 430 and a swivel portion 432. The main body 430 includes the clamp face with recesses for capturing the fixation elements and a transverse groove. The swivel portion 432 comprises a cylindrical outer clamp face 434 having some similarities to the cylindrical outer clamp face 132 of the inner jaw 126 described above. For example, the outer clamp face 434 is arranged to interface with the saddle assembly 406 to prevent relative pivoting about the pitch axis 30*a*. A transverse bore in the swivel portion 432 includes a counter bore and is arranged to receive an axle as described below. The outer clamp face 434 includes a saddle assembly receiving area 436. This is similar in many ways to the saddle assembly receiving areas described above because it is configured to interface with the saddle assembly 406 and configured to offset interdigitations on the saddle assembly 406 from interdigitations on the inner jaw 424 to permit swiveling. A slot-like opening 438 is formed in the saddle assembly receiving area 436. This opening intersects the transverse bore, creating a substantially hollow swivel portion 432. In the example shown, the opening extends about 120 degrees around the cylindrical surface of the saddle assembly receiving area 436, providing a pivot range of about 120 degrees.

The saddle assembly 406 includes shoes 440, a first saddle 442, a first biasing element as a wave spring 444, a second biasing element as a coil spring 446, and a second saddle 448.

The shoe 440*a* is configured to interface with the saddle assembly receiving area 436 of the swivel portion 432. Accordingly, these have smooth concave surfaces configured to receive the cylindrical shape of the saddle assembly receiving area 436. In this example, the shoes 440 are rectangular. Their shape also cooperates with the saddle assembly receiving area 436 to reduce relative pivoting of the clamps relative to the respective shoes. The shoes 440 each include a central through hole through which the stud 416 extends. As can be seen in the cross-sectional view in FIGS. 12 and 13, the shoes 440 include a counter bore 449 aligned with the through hole. The counter bore 449 receives the coil spring 446, which biases the shoes 440*a*, 440*b* apart from one another, thereby biasing the clamps 102, 104 apart from each other and from the saddles 442, 448. As discussed, any type of biasing elements may be used.

The first and second saddles 442, 448 are similar in many ways to those described above and not all the features will be repeated there. Even still, the saddles 442, 448 differ from those described above because they are formed with shoe-receiving portions 450 in place of the leaf spring seats 242. These shoe receiving portions 450 receive the non-circular shoes and limit the relative rotation of the first and second saddles 442, 448 to their respective shoes 440 the saddles 442, 448 also includes through holes sized to permit passage of the stud 416 and the coil spring 446, which is disposed about the stud 416.

The wave spring 444 is disposed between the first and second saddles 442, 448 and biases the saddles 442, 448 apart. When the wave spring 444 is compressed by the locking nut 412, the interdigitations on the saddles engage and the saddles are prevented from relative rotation about the yaw axis 40.

The swivel element 408 connects the rod and pin clamps 402, 404 and permits swiveling of the clamps. Similar to the stud 116 described above, the stud 416 includes a distal end with a transverse bore sized to receive the axle 418. The transverse bore therefore forms an axle seat. The proximal end is threaded to receive the locking nut 412. In the example shown, the proximal end includes a reverse threaded small-diameter tip with an additional lock nut 470 disposed thereon. The lock nut 470 and the reverse threads prevent inadvertent removal of the locking nut 412.

The axle 418 in this embodiment includes a head portion 460 having a larger diameter and an axle body 462 having a smaller diameter. The head portion 460 is received into the counter bore in the transverse bore in the swivel portion 432. As can be seen in the cross-sectional views in FIG. 13, the axle's body portion passes through the hole in the distal end of the stud. In one embodiment, the stud 416 swivels about the axle 418 and the axle is press fit, threaded, pinned, or otherwise secured in the transverse bore. In another embodiment, the stud 416 is fixed to the axle 418 and the axle pivots or swivels relative to the swivel portion 432 of the inner jaw 424.

Figure 14B:
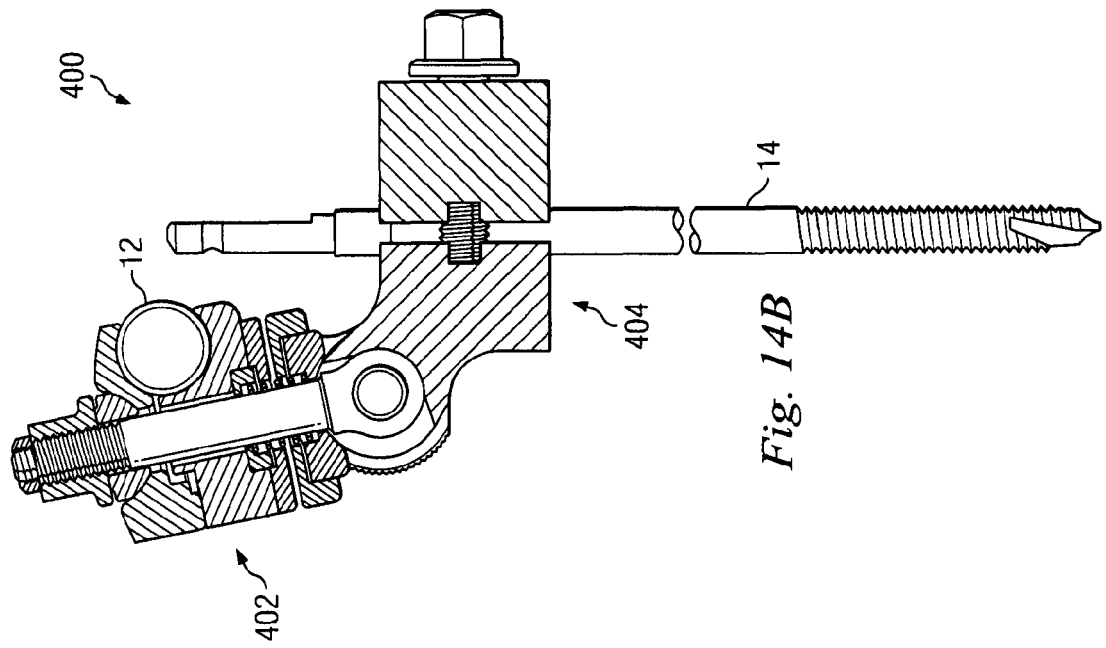
FIGS. 14A and 14B are illustrations with a first clamp rotated relative to a second clamp to its extreme positions.
Figure 14A:
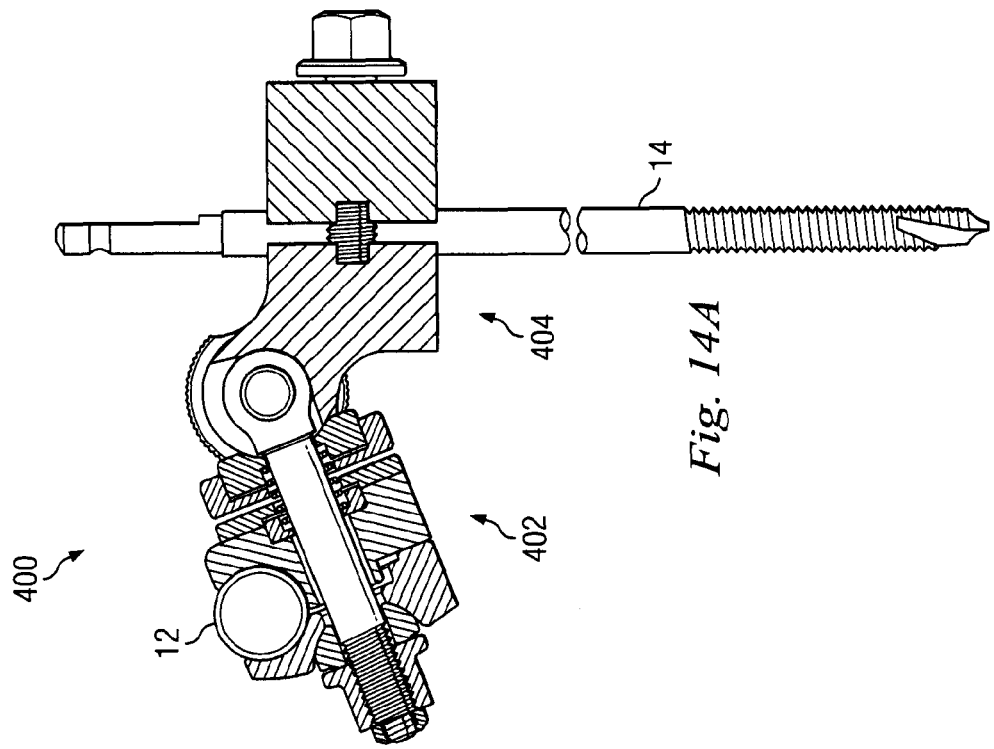

FIGS. 14A and 14B show cross-sectional views of the clamping device 400 with the rod 12 and the pins 14 swiveled about the pitch axis 30a between ends of the swivel range. As can be seen, the clamping device 400 is configured to swivel within a range of about 110 degrees. In some embodiments, the range of pivot range may about 50 degrees or greater. In other embodiments, the pivot range may be about 90 degrees or greater. In other examples, the pivot range may about 120 degrees or greater, and in one embodiment, to 150 degrees or greater. Other ranges are contemplated. Swiveling in this manner provides a larger swivel range than has been provided previously. Accordingly, the additional range of motion enables a surgeon to more easily set up and manipulate fixation frames.

As described above, in order to accommodate the higher swivel range, the radius formed by the outer clamp face 434 on the inner jaw 424 is smaller than the radius formed by the outer clamp face on the bar clamp 402.

A surgeon places the clamping device 400 in the open position by loosening the locking nut 112 and loosening the locking components associated with the multi-pin clamp 404. In this condition the helical wave spring 444 biases the saddles 442, 448 apart, and the coil spring 446 biases the shoes 440a, 440b apart, thereby separating the inner jaws from the respective saddles 442, 448. The surgeon may then introduce a fixation element into each of the rod and pin clamps. Insertion of the rod into the bar clamp 402 may separate the jaws of the clamp 402 and compress the coil spring 446 slightly. Once the fixation rod is within the passage between the jaws, the biasing coil spring 446 may bias the jaws toward each other to provisionally secure the fixation rod. Likewise, pins inserted into the multipin clamp may compress the springs associated with the locking components of the pin clamp 404. With the fixation elements captured between the jaws, the clamping device 400 is in a provisionally locked condition. That is, the fixation elements are provisionally secured within the respective clamps between the outer and inner jaws. In this position, the clamping device and fixation elements may be manipulated as desired to build the fixation frame and align bone tissues as desired. As discussed above, this may include manipulating the multi-pin clamp 104 about the pitch axis 30a over a large pivot range.

Once the pins and bars are in a desired position, the surgeon locks the clamping device 400 against further movement. This is done by tightening the bolts forming the locking components 428 associated with the multi-pin clamp 404. The nut 412 is then tightened on the bar clamp 404. This draws the inner jaw 424 of the pin clamp 404 toward the locking nut 412. As the nut is tightened, the wave spring 444 compresses, and the interdigitations on the saddles provide positive retention from relative planar rotation. In addition, the coil spring compresses so that the splines on the inner jaws engage the splines on the concave sides of the saddles 442, 448, and the spherical washer 410 tightens against the outer jaw 422 of the bar clamp 402. This tightens the outer jaw 422 against the fixation element to more tightly secure it in place between the jaws. Thus, in a fully locked state, the clamping device 400 is locked against all relative movement of the clamps, including releasing the fixation element.

Figure 15:
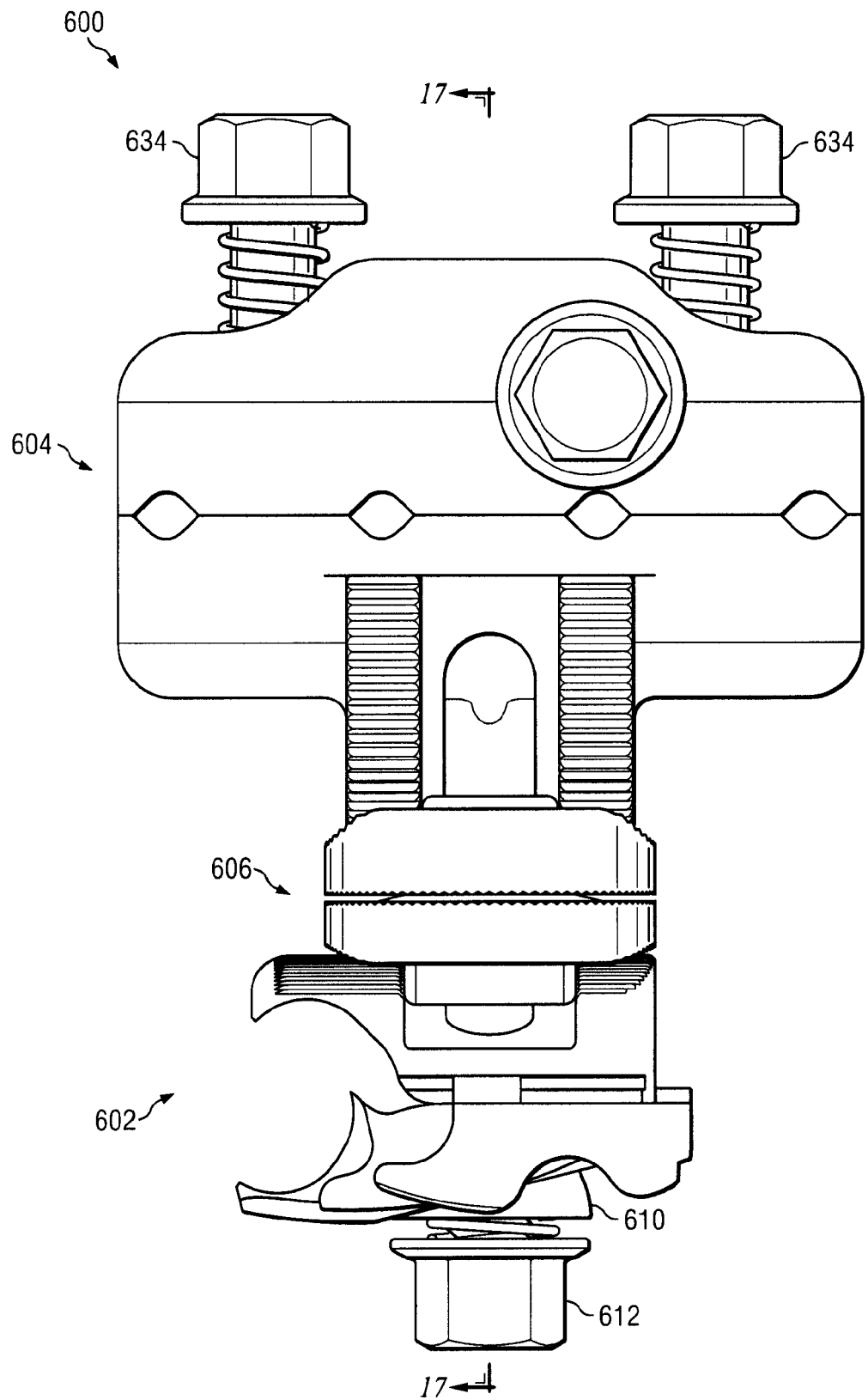
FIG. 15 is an illustration of another exemplary external fixation system in accordance with one exemplary aspect of the present disclosure.
Figure 16:
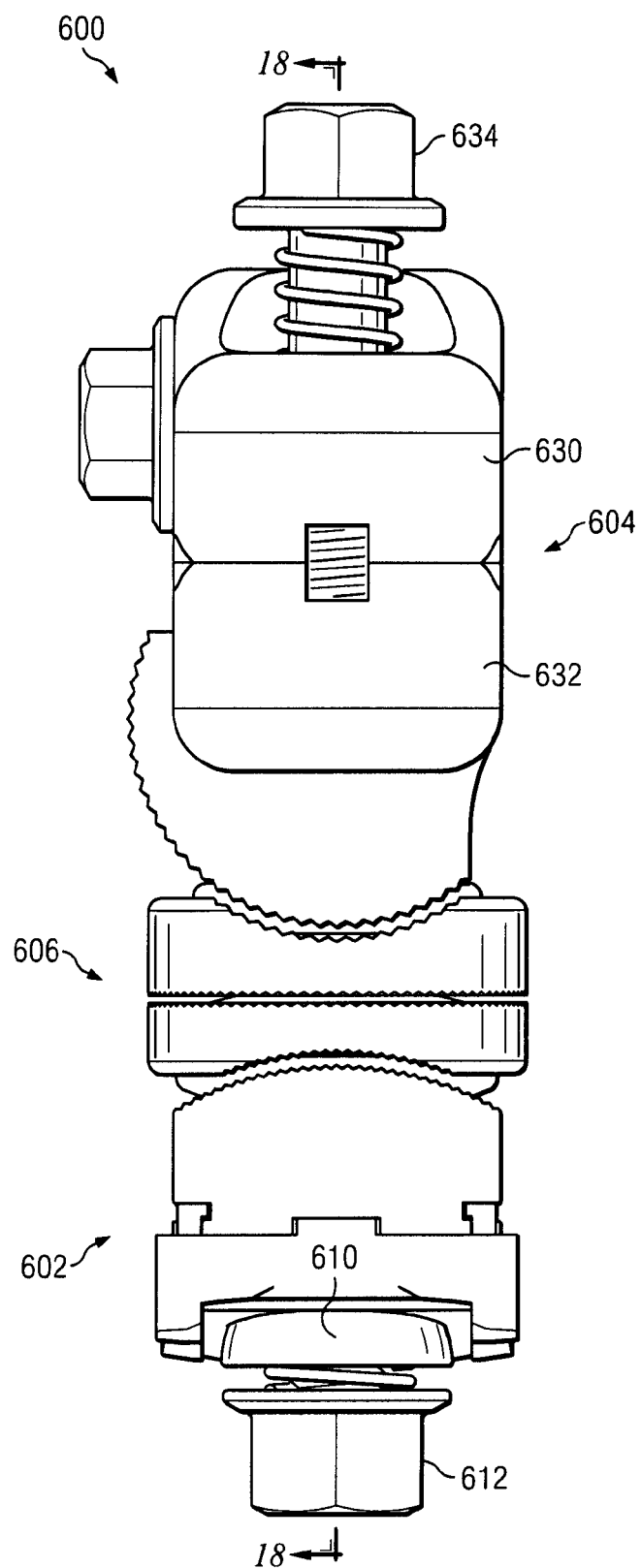
FIG. 16 is an illustration of a side view of the clamping device of FIG. 15.
Figure 17:
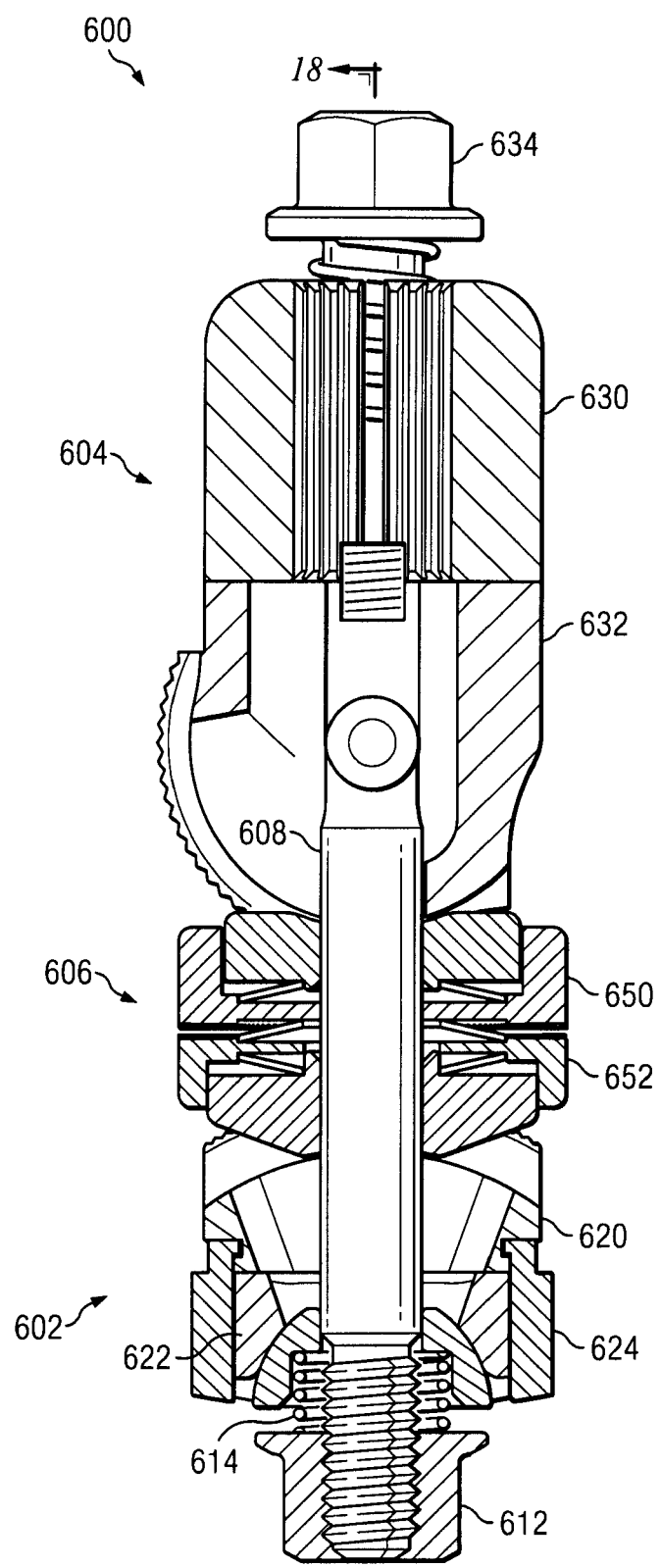
FIG. 17 is an illustration of a cross-sectional view of the clamping device of FIG. 15.
Figure 18:
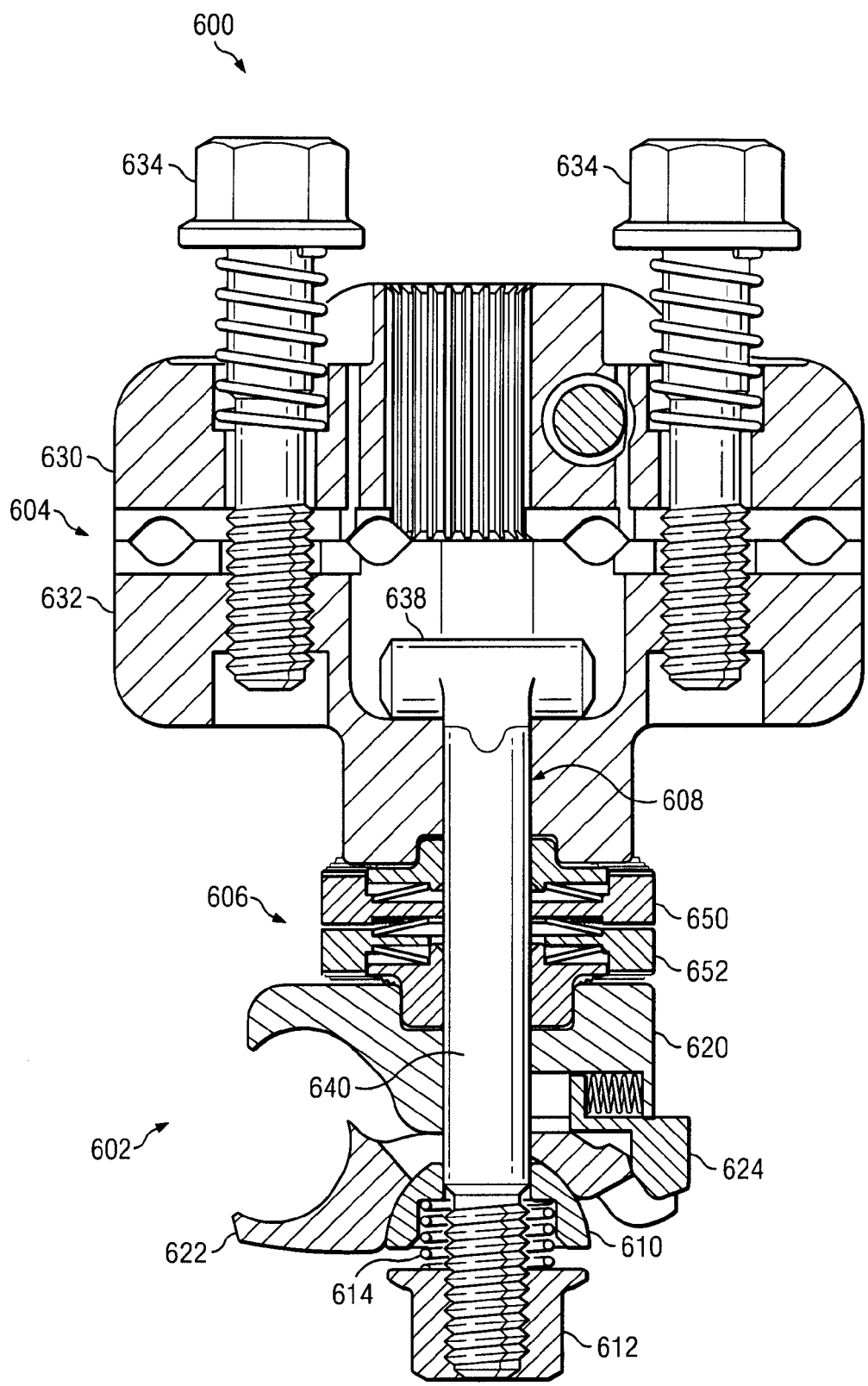
FIG. 18 is an illustration of a cross-sectional view of the clamping device of FIG. 15 taken transverse to the cross-sectional view in FIG. 17.

FIGS. 15-18 show a third embodiment of a clamping device, referenced herein by the numeral 600. FIG. 15 is a front view, FIG. 16 is a side view, and FIGS. 17 and 18 are cross-sectional views. Much of the discussion above apples equally to the clamping device 600, and will not be repeated in detail here. The clamping device 600 includes a bar clamp 602, a multi-pin clamp 604, and a saddle assembly 606. The clamping device 600 also includes a locking nut 612, a spherical washer 610, and a biasing element 614.

The bar clamp 602 includes an inner jaw 620, an outer jaw 622, and in this example, a latch 624. Such a clamp is described in detail in incorporated U.S. patent application Ser. No. 13/175,343, titled Multi-Locking External Fixation Clamp, filed Jul. 1, 2011.

The pin clamp 604 in this embodiment is made up of an outer jaw 630, an inner jaw 632, and a locking component 634 including biasing elements as springs and including bolts. The bolts are clamping elements that are threaded into the inner jaw 632 and tighten down on the outer jaw 630. Both the top surface of the inner jaw 632 and bottom surface of the outer jaw 630 are configured to hold two or more external fixation elements, such as the bone pins 14 discussed above. In this example, helical wire spring biasing elements are included. Other embodiments, however, do not include these biasing elements or include alternative biasing elements.

A swivel element 608 has an axle 638 and a stud 640. The bar clamp 602 is free to rotate about the stud 640. The inner jaw 632 of the pin clamp 604 has a blind slot configured to hold the axle 638 and has a through slot to allow passage of the stud 640 while the swivel element is rotated about the pin clamp 604.

The saddle assembly 606 includes a first saddle 650, a second saddle 652, shoes as discussed above, and biasing elements as spring washers. The through slot on the inner jaw 632 extends through a saddle assembly receiving area that acts against a shoe of the saddle assembly. When the washer springs are compressed, the inner jaw 632 acts against the first saddle 650. In turn, the saddle 650 acts against the second saddle 652 associated with the bar clamp 602. The swivel element 608 can be articulated in the slot in this embodiment a total of 80 degrees. Tightening the nut 612 clamps the jaws of the bar clamp 602 onto the designated external fixation element, tightens the inner jaw 620 against the saddle 652 to lock angulation, tightens the saddles 650, 652 together to stop rotation, and tightens the saddle 650 to the inner jaw 632 of the pin clamp 604 to lock the swivel 608 assembly from further swiveling.

In the example shown, the stud 640 of the swivel element 608 has a longitudinal axis that defines a yaw axis, about which the bar clamp 602 can rotate relative the pin clamp 604. The pin clamp 604 is fixed to the swivel element 608 in a manner that it does not rotate about the yaw axis, but instead moves with the swivel element 608.

The axle 638 of the swivel element 608 has an axis transverse to the longitudinal axis of the stud 640. At least the inner and outer jaws 632, 630 of the pin clamp 604 can rotate about the axle axis. The bar clamp 602 is fixed to the swivel element 608 in a manner that it does not rotate about the axle axis, but instead moves with the swivel element 608.

The inner jaw 620 of the bar clamp 602 cooperates with the saddle 652 having a concave surface forming a pitch axis transverse to the stud axis. This pitch axis is also transverse to the axis of a fixation element, such as a fixation rod, that may be gripped by the bar clamp 602.

In the example shown, the inner jaw 632 of the pin clamp 604 has splines that interdigitate with corresponding splines on the saddle 650. In addition the inner jaw 620 of the bar clamp 602 includes splines on its concave surface that interdigitate with corresponding splines on the saddle 652. In some examples, the saddle 650 and the saddle 652 each include radially projecting splines that that interdigitate with each other.

In some examples, other types are provided. For example, some embodiments do not use entirely separate components for the inner and outer jaws forming a single clamp. In some embodiments, the inner and outer jaws of a single clamp are connected by a flexible portion that permits the jaws to open and close by flexing. That is, the jaws may be one-piece jaws connected via a flexible portion that allows the jaws to flex to receive and clamp on a fixation element. Other types of clamps and jaws are also contemplated.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A clamping device for an external fixation system, comprising:
    a first clamp having an opening for receiving an external fixation element, the first clamp having an axle seat and comprising an inner jaw and an outer jaw, the inner jaw comprising a one-piece inner jaw;
    a first base component having a concave first surface and having a second surface facing away from the first surface, the concave surface being in selective engagement with the first clamp; and
    a swivel element comprising an axle component and a post component, the axle seat being disposed inside the inner jaw, the axle component being disposed on the axle seat, the post component extending from the axle component and having a length sized to extend from the axle component through a second external fixation clamp, the post component being arranged to swivel relative to the axle seat.

2. The clamping device of claim 1, wherein the first clamp includes a first convex outer surface arranged to interface with the concave first surface of the first base component, the first convex outer surface and the concave first surface comprising friction enhancing features.

3. The clamping device of claim 2, wherein the friction enhancing features are splines.

4. The clamping device of claim 1, wherein the axle component and the post component are rigidly fixed.

5. The clamping device of claim 1, wherein the post component is configured to pivot about the axle component.

6. The clamping device of claim 1, wherein the post component is configured to extend from the axle component in a direction away from the outer jaw.

7. The clamping device of claim 1, further comprising a second external fixation clamp.

8. The clamping device of claim 7, wherein the second clamp is secured to the post component and the second clamp can be locked in the desired angle relative to the first clamp.

9. The clamping device of claim 7, further comprising a second base component disposed between the first base component and the second clamp.

10. The clamping device of claim 7, wherein at least one of the first and second clamps is configured to hold a plurality of fixation elements.

11. The clamping device of claim 1, wherein the swivel element and the first clamp cooperate to permit the post to swivel through a swivel range greater than fifty degrees.

12. The clamping device of claim 1, wherein the first clamp comprises a tightening mechanism independent of the swivel element.

13. The clamping device of claim 12, wherein the first clamp comprises an inner jaw and an outer jaw, and wherein the tightening mechanism comprises a tightening post extending from one of the inner and outer jaws through the other of the inner and outer jaws.

14. The clamping device of claim 13, wherein the tightening post is integral with the inner jaw.

15. The clamping device of claim 1, wherein the inner and outer jaws are one-piece first and second jaws connected via a flexible portion that allows the first and second jaws to flex to receive and clamp onto the fixation element.

16. The clamping device of claim 15, wherein the clamping device comprises a second clamp having an opening for receiving a second external fixation element, the second clamp being configured to swivel relative to the axle seat with the post component, the second clamp having one-piece third and fourth jaws connected via a flexible portion that allows the third and fourth jaws to flex to receive and clamp onto a second fixation element.

17. A clamping device for an external fixation system, comprising:
    a first clamp having an opening for receiving a first external fixation element, the first clamp comprising an inner jaw and an outer jaw, the inner jaw comprising a one-piece inner jaw having an axle seat;
    a second clamp having an opening for receiving a second external fixation element; and
    a swivel element comprising an axle component and a post component, the axle component being disposed on the axle seat, the post component extending from the axle component through the second clamp, the post component and the second clamp being arranged to swivel in a single plane relative to the axle seat.

18. The clamping device of claim 17, further comprising a locking mechanism associated with the post component, the locking mechanism being configured to lock a second fixation element in the second clamp while not locking a first fixation element in the first clamp.

19. The clamping device of claim 17, wherein the first clamp comprises a tightening mechanism independent of the swivel element.

20. The clamping device of claim 19, wherein the tightening mechanism comprises a tightening post extending from the one of the inner and outer jaws through the other of the inner and outer jaws.

21. A clamping device for an external fixation system, comprising:

a first clamp having an opening for receiving a first external fixation element, the first clamp comprising an inner jaw and an outer jaw, the inner jaw having an axle seat;

a second clamp having an opening for receiving a second external fixation element;

a swivel element comprising an axle component and a post component, the axle component being disposed on the axle seat, the post component extending from the axle component through the second clamp, the post component and the second clamp being arranged to swivel in a single plane relative to the axle seat, wherein the inner and outer jaws are one-piece first and second jaws connected via a flexible portion that allows the first and second jaws to flex to receive and clamp onto the first fixation element.

22. The clamping device of claim 21, wherein the second clamp comprises one-piece third and fourth jaws connected via a flexible portion that allows the third and fourth jaws to flex to receive and clamp onto the second fixation element.

23. A clamping device for an external fixation system comprising:

a first clamp comprising a first jaw and a second jaw, the first and second jaws cooperating to capture a fixation element, one of the first and second jaws having a hollow interior portion comprising an axle seat, the one of the first and second jaws comprising a one-piece jaw;

a second clamp comprising a third jaw and a fourth jaw, the third and fourth jaws cooperating to capture a fixation element; and a swivel element having an axle disposed in the hollow interior portion on the axle seat and having a post component extending from the hollow interior portion through the second clamp, the second clamp being configured to rotate about an axis coincident with the post, and the second clamp and the post component being configured to rotate about an axis coincident with the axle.

24. The clamping device of claim 23, comprising a tightening component associated with the second clamp configured such that the act of tightening the tightening component locks the second clamp as well as the rotation about the post axis and rotation about the axle.

25. The clamping device of claim 23, comprising a base component disposed between the first and second clamps.

26. The clamping device of claim 25, wherein the first jaw has a convex surface with splines thereon, the splines interdigitating with opposing splines on the base component.

27. The clamping device of claim 23, wherein at least one of the first and second clamps are configured to hold more than one external fixation element.

28. The clamping device of claim 23, wherein the first and second jaws are combined one-piece jaws connected via a flexible portion that allows the first and second jaws to flex to receive and clamp onto the fixation element.

29. A clamping device for an external fixation system comprising:

a first clamp comprising a first jaw and a second jaw, the first and second jaws cooperating to capture a fixation element, one of the first and second jaws having a hollow interior portion comprising an axle seat;

a second clamp comprising a third jaw and a fourth jaw, the third and fourth jaws cooperating to capture a fixation element;

a swivel element having an axle disposed in the hollow interior portion on the axle seat and having a post component extending from the hollow interior portion through the second clamp, the second clamp being configured to rotate about an axis coincident with the post, and the second clamp and the post component being configured to rotate about an axis coincident with the axle;

a first base component disposed between the first and second clamps; and a second base component having one of a concave and a convex surface, the third jaw having the other of the concave and convex surface and a receiving area forming a bearing surface allowing the second clamp to rotate about an axis transverse to the post axis.

30. The clamping device of claim 29, where the third jaw comprise splines and the second base component comprises splines that interdigitate with the splines on the third jaw.

31. The clamping device of claim 29, where the second base component comprises radial splines that interdigitate with radial splines on the first base component.

32. The clamping device of claim 31, wherein the third and fourth jaws are combined one-piece jaws connected via a flexible portion that allows the third and fourth jaws to flex to receive and clamp onto the fixation element.

* * * * *